(12) United States Patent
Burbank et al.

(10) Patent No.: US 9,017,273 B2
(45) Date of Patent: Apr. 28, 2015

(54) DEVICES AND METHODS FOR TREATING RESTLESS LEG SYNDROME

(75) Inventors: Fred Burbank, Laguna Niguel, CA (US); Mike Jones, San Clemente, CA (US); Al Memmolo, Carlsbad, CA (US)

(73) Assignee: Sensory Neurostimulation, Inc., San Clemente, CA (US)

( * ) Notice: Subject to any disclaimer, the term of this patent is extended or adjusted under 35 U.S.C. 154(b) by 1023 days.

(21) Appl. No.: 12/396,358

(22) Filed: Mar. 2, 2009

(65) Prior Publication Data
US 2009/0221943 A1    Sep. 3, 2009

Related U.S. Application Data

(60) Provisional application No. 61/032,571, filed on Feb. 29, 2008.

(51) Int. Cl.
*A61H 23/00* (2006.01)
*A61H 1/02* (2006.01)
(Continued)

(52) U.S. Cl.
CPC ....... *A61H 1/0237* (2013.01); *A61F 2007/0071* (2013.01); *A61F 2007/0075* (2013.01);
(Continued)

(58) Field of Classification Search
CPC ..... A61H 23/00; A61H 23/02; A61H 23/008; A61H 2201/165; A61H 2201/5097; A61H 1/0237; A61H 1/0255; A61H 1/0266; A61H 1/008
USPC .......... 601/33, 34, 46–49, 56–58, 66, 67, 70, 601/71, 78, 79, 84, 107
See application file for complete search history.

(56) References Cited

U.S. PATENT DOCUMENTS

| | | | | |
|---|---|---|---|---|
| 5,437,607 A | * | 8/1995 | Taylor | 601/49 |
| 5,759,198 A | * | 6/1998 | Karell | 607/48 |

(Continued)

FOREIGN PATENT DOCUMENTS

| | | |
|---|---|---|
| EP | 0372114 | 6/1990 |
| FR | 2608918 | 7/1988 |

(Continued)

OTHER PUBLICATIONS

Thorpy, Michael J., "New paradigms in the treatment of restless leg syndrome", Neurology Jun. 2005: 64 (Suppl 3) : S28-33.*

(Continued)

*Primary Examiner* — Justine Yu
*Assistant Examiner* — Latoya M Louis
(74) *Attorney, Agent, or Firm* — K. David Crockett, Esq.; Crockett & Crockett, PC

(57) ABSTRACT

An exemplary system for generating a counter-stimulation in a patient suffering from RLS includes a device configured and arranged to generate a counter-stimulation in a patient suffering from RLS, the counter-stimulation of an amplitude, intensity, and time duration lower than that which would wake the patient and higher than that sufficient to relieve RLS, or sufficient to relieve RLS symptoms and allow the patient to return to sleep, a controller configured and arranged to drive the counter-stimulation generation device, the controller being in communication with the counter-stimulation device, and a base configured and arranged to hold the counter-stimulation generation device adjacent to a patient, the counter-stimulation device attached to the base. An exemplary method of treating RLS includes selecting a patient experiencing RLS, and stimulating a portion of the patient at an amplitude, intensity, and duration sufficient to act as a counter-stimulation to RLS.

25 Claims, 20 Drawing Sheets

(51) Int. Cl.
*A61H 1/00* (2006.01)
*A61H 7/00* (2006.01)
*A61H 9/00* (2006.01)
*A61H 15/00* (2006.01)
*A61H 23/02* (2006.01)
*A61N 1/36* (2006.01)
*A61F 7/00* (2006.01)
*A61F 7/02* (2006.01)
*A61N 2/00* (2006.01)

(52) U.S. Cl.
CPC ......... A61F2007/0296 (2013.01); *A61H 1/008* (2013.01); *A61H 1/0255* (2013.01); *A61H 1/0266* (2013.01); *A61H 7/001* (2013.01); *A61H 7/004* (2013.01); *A61H 9/0078* (2013.01); *A61H 9/0092* (2013.01); *A61H 15/0078* (2013.01); *A61H 23/0218* (2013.01); *A61H 23/0263* (2013.01); *A61H 2015/0014* (2013.01); *A61H 2201/0142* (2013.01); *A61H 2201/02* (2013.01); *A61H 2201/0228* (2013.01); *A61H 2201/0242* (2013.01); *A61H 2201/0257* (2013.01); *A61H 2201/0285* (2013.01); *A61H 2201/10* (2013.01); *A61H 2201/105* (2013.01); *A61H 2201/165* (2013.01); *A61H 2203/0456* (2013.01); *A61H 2205/10* (2013.01); *A61H 2205/106* (2013.01); *A61H 2205/108* (2013.01); *A61H 2205/12* (2013.01); *A61N 1/36021* (2013.01); *A61N 2/00* (2013.01); *A61H 2201/1215* (2013.01); *A61H 2201/1642* (2013.01); *A61H 2201/1676* (2013.01)

(56) References Cited

U.S. PATENT DOCUMENTS

| | | | | |
|---|---|---|---|---|
| 6,093,164 | A * | 7/2000 | Davis et al. | 602/62 |
| 6,146,342 | A | 11/2000 | Glen | |
| 6,155,976 | A * | 12/2000 | Sackner et al. | 600/300 |
| 6,505,361 | B1 * | 1/2003 | Ogawa | 5/109 |
| 7,147,610 | B2 * | 12/2006 | Maalouf | 601/15 |
| 7,462,158 | B2 * | 12/2008 | Mor | 601/46 |
| 7,551,100 | B1 * | 6/2009 | Salley et al. | 340/692 |
| 7,578,013 | B2 * | 8/2009 | Aikman | 5/632 |
| 2003/0176822 | A1 | 9/2003 | Morgenlander | |
| 2006/0252566 | A1 * | 11/2006 | Gibree | 472/118 |
| 2007/0085286 | A1 * | 4/2007 | Gibree | 280/47.38 |
| 2007/0255187 | A1 * | 11/2007 | Branch | 601/15 |
| 2009/0048075 | A1 * | 2/2009 | Quarz | 482/57 |
| 2009/0112134 | A1 * | 4/2009 | Avni | 601/15 |
| 2009/0143704 | A1 * | 6/2009 | Bonneau et al. | 600/595 |

FOREIGN PATENT DOCUMENTS

| | | |
|---|---|---|
| JP | 10-099391 | 4/1998 |
| JP | 2001-087331 | 4/2001 |
| JP | 2003-079688 | 3/2003 |
| WO | WO98/29996 | 9/1998 |
| WO | WO98/56331 | 12/1998 |
| WO | WO00/64598 | 11/2000 |
| WO | WO2004/110333 | 12/2004 |

OTHER PUBLICATIONS

Ondo, William G., "Pain in Restless Legs Syndrome", www.rls.org Summer 2011; pp. 15-16.*

Mayo Clinic staff "Restless legs syndrome", Mayo Clinic Jan. 2012; pp. 1-10.*

"Restless Legs Syndrome Fact Sheet", http://www.ninds.nih.gov/disorders/restless_legs/detail_restless_legs.htm, NINDS, Sep. 2010 NIH Pub. No. 10-4847.*

Partial International Search Report for PCT Patent App. No. PCT/US2009/035765 (Jun. 15, 2009).

Notification of Reasons for Refusal for Japanese Patent App. No. 2010-548937 (Aug. 20, 2012) with English language translation thereof.

Eliasson, A. H., et al., "Sequential Compression Devices for Treatment of Restless Legs Syndrome," Medicine 2007;86(6):317-323, Lippincott Williams & Wilkins.

Lettieri, C. J., et al., "Pneumatic Compression Devices Are an Effective Therapy for Restless Legs Syndrome: A Prospective, Randomized, Double-Blinded, Sham-Controlled Trial," Chest 2009;135:74-80, American College of Chest Physicians, US.

Mitchell, U. H., et al., "Comparison of two infrared devices in their effectiveness in reducing symptoms associated with RLS," Physiotherapy Theory and Practice, Early Online, 2010, pp. 1-8, Informa Healthcare USA, Inc.

Mitchell, U. H., et al., "Restless legs syndrome and near-infrared light: An alternative treatment option," Physiotherapy Theory and Practice, Early Online, 2010, pp. 1-7, Informa Healthcare USA, Inc.

Montagna, P., et al., "Clonazepam and vibration in restless legs syndrome," Acta Neurol. Scand. 1984;69:428-430, Wiley-Blackwell.

* cited by examiner

SECTION A-A

SECTION A-A

SECTION A-A

SECTION A-A

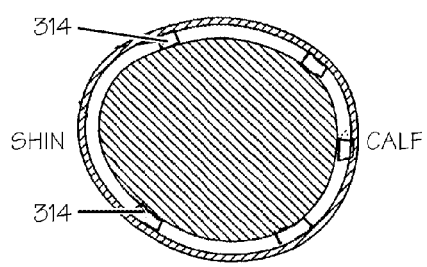
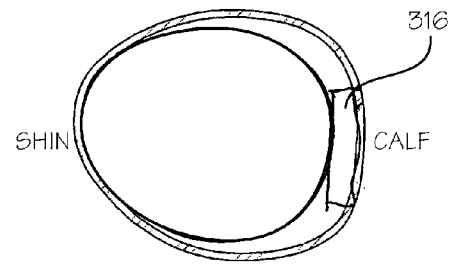
Fig. 39    Fig. 40
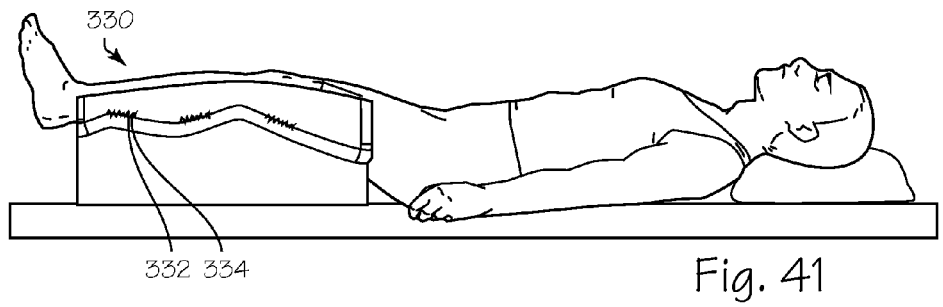
Fig. 41
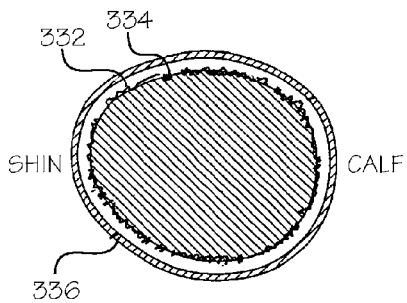
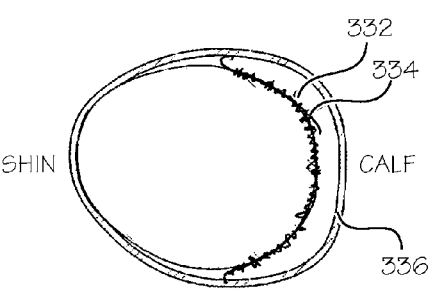
Fig. 42    Fig. 43
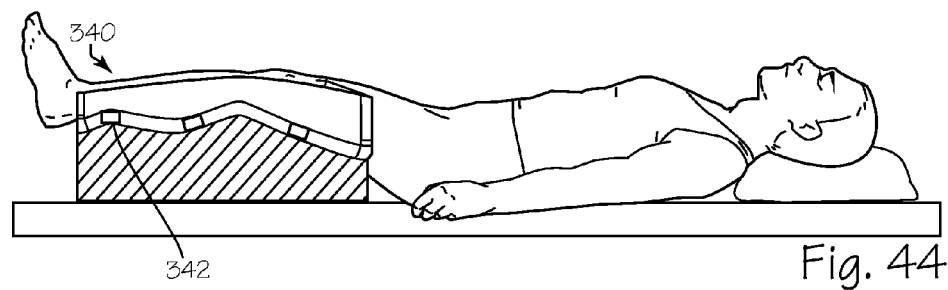
Fig. 44

SECTION A-A

SECTION A-A

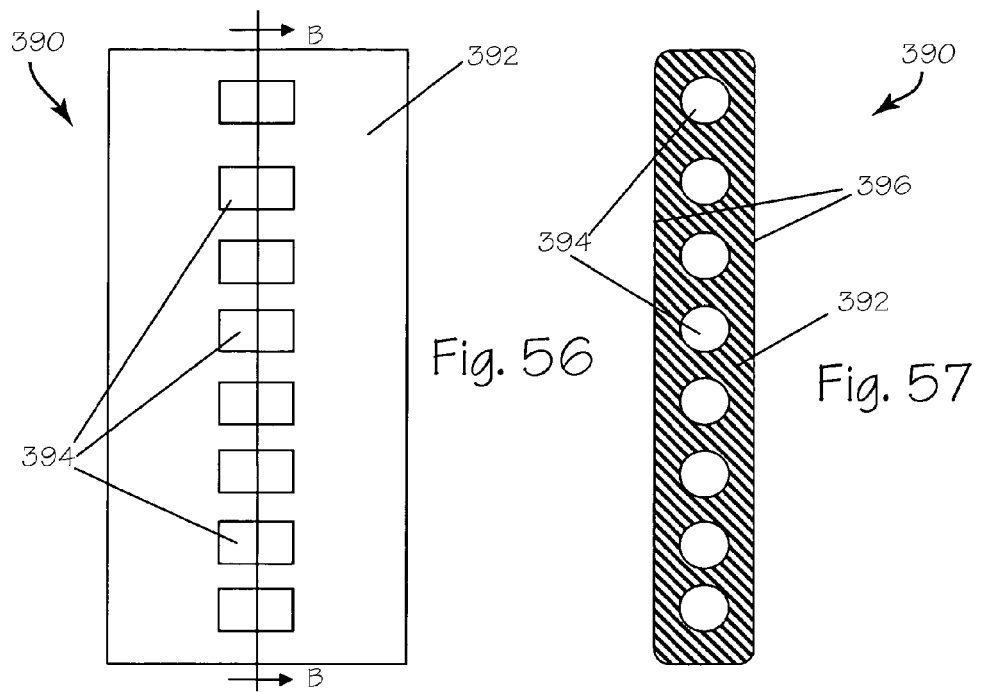
Fig. 56
Fig. 57
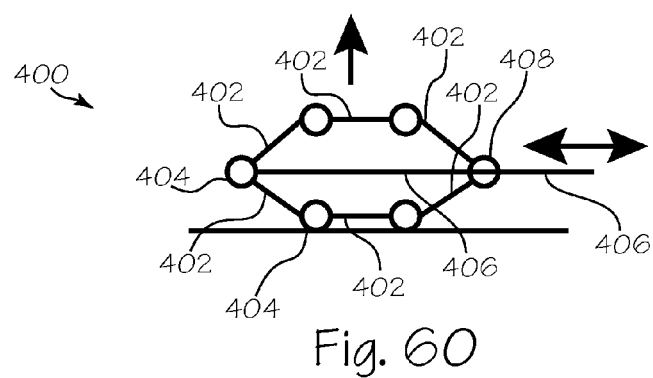
Fig. 60

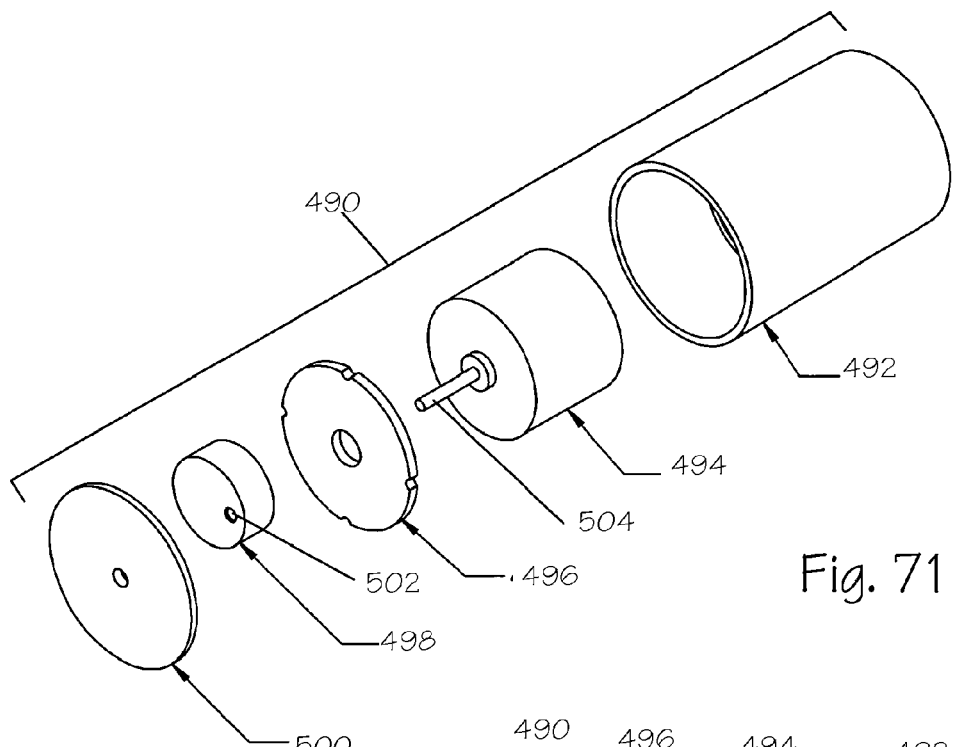
Fig. 71
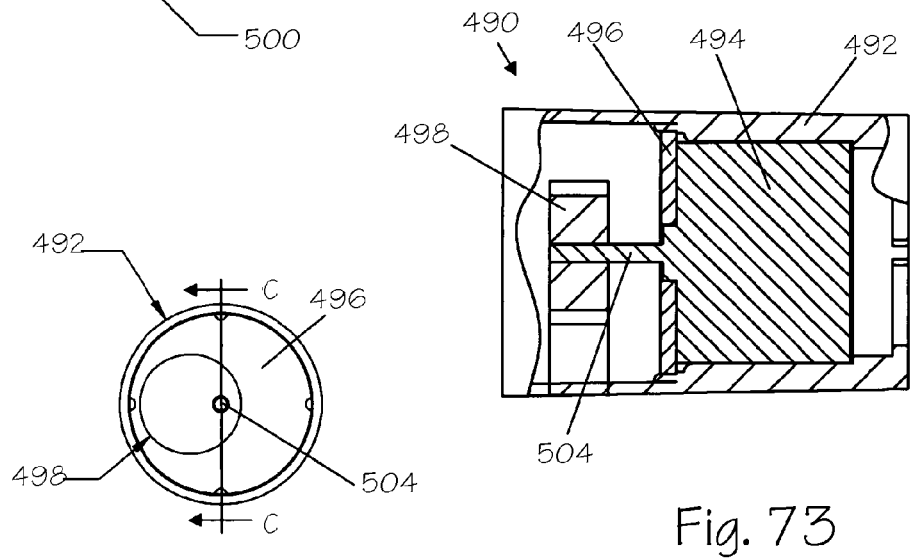
Fig. 72
Fig. 73

DEVICES AND METHODS FOR TREATING RESTLESS LEG SYNDROME

This application claims priority under 35 U.S.C. §119 to U.S. Provisional application No. 61/032,571, filed 29 Feb. 2008, the entirety of which is incorporated by reference herein.

BACKGROUND

1. Field of Endeavor

The present invention relates to devices, systems, and processes useful to treat Restless Leg Syndrome.

2. Brief Description of the Related Art

In 1685 Thomas Willis, an 17th century English physician, published the first description of what we now term "restless legs syndrome" ("RLS").(1,2) He characterized patients with this disorder as, "Wherefore to some, when being a bed they betake themselves to sleep, presently in the Arms and Legs Leapings and Contractions of the Tendons, and so great a Restlessness and Tossing of their Members ensure, that the diseased are no more able to sleep, than if they were in a Place of greatest Torture." In 1945, Karl Axel Ekbom coined the term "restless legs syndrome" and suggested a neurological instead of a psychiatric origin to the disorder.(3) Ekbom focused attention on the abnormal sensory component of the disease.

With development of "Sleep Labs" in the 1970's, the sleep-robbing nature of RLS was objectively characterized.(4) In 1990 the American Sleep Disorders Association defined RLS as (i) disagreeable touch sensations seemingly originating in the legs, that (ii) come upon some nights and not other nights, and that (iii) are relieved almost immediately upon standing or walking. In 1999, a task force of the American Academy of Sleep Medicine summarized the then current understanding of RLS.(5) Diagnostic criteria were further expanded in 1995 and 2004 by international groups to include episodes occurring during the daytime when drowsy.(6,7)

Disagreeable touch sensations were cataloged as "creepy-crawly, ants crawling, jittery, pulling, worms moving, soda bubbles in veins, electric shock, pain, the gotta moves, burning, jimmy legs, hebbie jeebies, tearing, throbbing, tight feeling, grabbing, Elvis legs, itching bones, crazy legs, and fidgets."(7) With symptom descriptions as bizarre as these, it is no wonder that early investigators lumped patients with RLS in with patients with psychiatric hysterical (conversion) disorders. However, clinical responses to various categories of (8) drugs and to iron therapy and the presence of at least two genetically identifiable phenotypes all argue in favor of a physical and not a psychological origin to RLS.(9)

RLS is a common disorder: prevalence of symptoms 5 or more nights per month were reported in 3% of individuals 18-29 years, 10% in 30-79 years, and 19% in those 80 or older.(10) Age adjusted prevalence in this study was 10%. In a similar study, prevalence was 11.5% with half of those reporting RLS symptoms causing moderate to very severe discomfort.(11) Others have described a rise in prevalence with age but have set peak prevalence at 70-79 years with a slight drop off in people 80 years and older.(12) Whatever the peak prevalence of RLS, it is more common in older individuals than younger and it severely affects emotional well-being in the elderly.(13,14)

A study of 23,000 individuals conducted in France, Germany, Spain, and the UK concluded that 11.1% of the general population have RLS and that in 50% of patients RLS symptoms significantly disrupted everyday activities and personal relationships.(15) A companion study of over 15,000 individuals determined that 5% of the population had RLS attacks at least twice weekly.(16) RLS is now sufficiently common that in the 2007 issue of Time Magazine it was featured in "The Year in Medicine from A to Z".(17) Although quite common, RLS is not commonly recognized by primary-care physicians even when a diagnostic description is given by the patient to his doctor.(18) However, when primary-care physicians are made aware of RLS, they can identify RLS in a high proportion of patients.(19,20)

RLS can be early in onset (before the age of 45) with slow progression of symptoms and run in families, or it can come on later in life, involving one member of a family with rapid development of severe symptoms.(12,21-24)

Because RLS is common, it has been observed in association with a wide variety of other disorders and diseases. Some have interpreted these associations as causal links. Such causal interpretations need to be viewed with great caution. The list includes metabolic and hormonal abnormalities, pregnancy, peripheral neuropathies, spinal and brainstem lesions, decreased serum magnesium and folate levels, anemia, rheumatoid arthritis, amyloidosis, carcinoma, musculoskeletal disease, anxiety, depression, multiple sclerosis, cognitive defects, hypertension, blood donors, heart disease, reduced libido, social isolation, gastroesophageal reflux, migraine headache, chronic lung disease, caffeine use, varicose veins, sleep apnea, gastric surgery, drug withdrawal, hypothyroidism, acute intermittent porphyria, arborizing telangiectasia, cholesterol microemboli, diabetes, periodic limb movement disorder in sleep (PLMS), somatoform pain disorder, being Caucasian, and more.(2,25-40,40-45)

However, by 2007, only two published studies of patients selected from the general population accurately measured the association of RLS with other disorders.(46,47) These two studies found that diabetes, reduced renal function, and anemia are significantly associated but make only a small contribution to the overall prevalence of RLS. Even in the older age groups where the RLS is most prevalent, secondary disorders and diseases increase RLS prevalence by only 10-20%.

Unlike these two general population studies, many small associative studies have identified patients with specific disorders or diseases and then compared RLS prevalence in these selected populations with the general population or with controls. In a review of 16 publications focused on patients with end-stage renal disease on dialysis published between 1991-2005, 15 (93.8%) of the 16 studies demonstrated higher prevalence rates in these dialysis patients than in the general population.(36) In one study, 84% of patients with end-stage renal disease had RLS. To support this association, it has been observed that in some patients, symptoms of RLS dramatically decrease following renal transplantation.(48) Like RLS in others, in dialysis patients RLS leads to poor sleep and thereby to a low quality of life.(49) Patients with RLS suffer from daytime sleepiness, depression, poor concentration, and even fear of long-distance travel during which their legs may become restless while awake.(9)

In a publication examining RLS and pregnancy, four studies demonstrated prevalence rates higher than the general population, while one showed rates no different that those observed in the general population.(36) Others have reported an association of RLS with pregnancy.(50) This association is further supported by the observation that the frequency of RLS attacks drops dramatically following childbirth.(51,52) Goodman et al. present a very convincing reverse "S" shaped-curve showing a dramatic decrease in RLS episodes following delivery.(53) In another study of pregnant women, an association was observed between RLS and parity.(47)

Women who had given birth to three or more children had a three times greater risk of having RLS compared to nulliparous women or to men.

Iron deficiency has been associated with RLS since 1945, although the connection between the two disorders is not clear-cut.(3,36,54) Correction of peripheral anemia does not always decrease RLS symptoms. Furthermore, most patients with RLS are not anemic. When studied by magnetic resonance imaging, iron abnormalities associated with RLS were observed in the substantia nigra of the brainstem.(55) Decreased serum ferritin (below 50 ng/mL) and cerebral spinal fluid ferritin levels have been associated with RLS.(2) Patients with RLS appear to have a decreased ability to transport iron into the central nervous system through the blood brain barrier.(56)

A wide variety of peripheral neuropathies have been connected with RLS including cryoglobulinemia, Charcot-Marie-Tooth ataxia type 2, diabetic, and amyloid types.(57-60)

To prospectively evaluate the concomitant occurrence of RLS and varicose veins in a population seeking treatment for varicose veins, and to assess the therapeutic response of RLS to sclerotherapy, 1397 patients with varicose veins were screened for RLS symptoms by questionnaire and interview. RLS symptoms were present in 312 (22%) of the 1,397 patients. Sclerotherapy with sodium tetradecyl sulphate was performed on 113 RLS patients. 111 (98.2%) of 113 treated patients reported initial relief from RLS symptoms. Follow-up showed recurrence rates of 8% and 28% at 1 and 2 years, respectively.(61)

And finally, RLS has been associated with the phenomenon of periodic leg movements in sleep (PLMS).(30) In 1953, Symonds described an involuntary clonic-like movement of the lower extremities that occurred during sleep, often waking the patient over and over again at night.(62) In 1965, Lugaresi et al. documented the presence of PLMS in patients with RLS.(63) In a polysomnographic study of 133 individuals with RLS, Montplaisir et al. observed PLMS in 80.2% of these individuals using a one-night's sleep PLMS index score of greater than 5 (one of the many definition of abnormal PLMS).(64) However, PLMS has also been observed in association with other forms of insomnia such as narcolepsy, rapid-eye-movement sleep disorder, and obstructive sleep apnea.(7) It has also been observed in normals.(7) Because RLMS is associated with many diseases and disorders and with normals, patients with RLS comprise only a fraction of patients with PLMS. At best the diagnosis of RLMS is "supportive" of the diagnosis of RLM; it is not diagnostic.

If RLS is caused by one of these associated disorder or disease, and if correction of the associated disorder or disease can stop the symptoms of RLS, then treatment is straight forward: treat the associated disorder or disease. Except for pregnancy and some forms of anemia, these associative disorders or diseases are not generally amenable to treatment. For most of these patients, palliation of RLS symptoms is the only treatment available.

On the other hand, in the vast majority of patients suffering from RLS, there is no associated disorder or diseases of the legs.(26) That is, in most individuals, RLS is idiopathic or primary in nature.(65) Their affected limbs are no different than limbs of people without RLS. Skin, muscles, bones, nerves, arterial or venous circulation, spinal reflexes, electromyography, nerve conduction studies, and imaging examination are all normal in patients with primary RLS.(12,52)

In patients with primary RLS, the anatomic site of origin of RLS appears to be in the central nervous system above the level of the spinal cord and below the level of the cerebral cortex.(12) The site of origin may be at the subcortical level, perhaps at the level of the thalamus and cerebellum.(66)

FIG. 1 includes an illustration showing a leg and the major classes of somatic sensory receptors, highly specialized cells associated with neurons that convert various forms of energy from physical stimuli into nerve impulses. The hairy skin H (including free nerve endings, nociceptors, Merkel's disks, and Ruffini's corpuscles), periosteum and interosseous membrane P (including Pacinian corpuscles), the gastrocnemius muscle, muscles M including muscle spindles, glabrous skin G (including free nerve endings, nociceptors, Merkel's disks, and Ruffini's corpuscles, and Meissner's corpuscles), joints J (including joint receptors), tendons and ligaments T (including Ruffini's corpuscles and Golgi tendon organs), and subcutaneous tissue S (including Pacinian corpuscles) are illustrated (67).

Whether secondary or primary, central to RLS is the nighttime onset of disagreeable somatic sensations that appear to originate in a leg or in legs. Of our five senses, touch is the most heterogeneous in character. Touch encompasses the sensation of pain and temperature, pressure and crude touch, fine or discriminatory touch, and vibratory sensation. A variety of specialized microscopic receptors or mechanical-electrical transducers are present in skin, subcutaneous tissues, muscles, tendons and ligaments, joints, and periosteum and interosseous membranes to distinguish different types of touch sensations, as shown in FIG. 1. These specialized transducers or filters include Pacinian corpuscles which are encapsulated, onion-like nerve coverings that sense deep pressure and vibrations in the 250-350 Hz range; Meissner's corpuscles which are oval structures surrounding nerve and located between dermal papillae and which detect pressure and low frequency vibration in the 30-50 Hz range; Merkel's discs which are spherical collection of cells that identify static pressure and respond to low frequency vibrations in the 5-15 HZ range; Ruffini's corpuscles which are elongated structures in the dermis that detect skin stretching and the sense of slipping; Golgi tendon organs, joint receptors, and muscle spindles that identify stretching, and free nerve endings that sense temperature and pain.(67)

Three distinct somatic sensory neuronal pathways exist for the legs. Each pathway begins in the leg and ends with a neuronal signals reaching the cerebral cortex and, hence, consciousness.

Pathway No. 1: When painful stimuli or changes in temperature excite the leg, they cause sensory nerves in skin to fire. These primary neurons then synapse in the ipsilateral dorsal horn of the spine with secondary neurons of the contralateral lateral spinothalamic tract. These lateral spinothalamic nerves then course up the spine reaching the thalamus on the opposite side of the stimulus. In the thalamus, these axons synapse with tertiary neurons that exit the thalamus and ascent in the internal capsule and terminate in the postcentral or sensory gyrus of the cerebral cortex.

Pathway No. 2: Pressure and crude touch nerves follow a similar pathway with the addition of fibers from the primary neuron for several spinal segments in the ipsilateral dorsal white matter column.

Pathway No. 3: Neurons that transmit the senses of fine or discriminatory touch, proprioception, and vibratory touch follow a different pathway to the thalamus. For the legs, the primary sensory neurons ascend in the ipsilateral fasciculus gracilis of the dorsal column of the spine to the ipsilateral nucleus gracilis in the medulla. In the nucleus gracilis these primary neurons synapse with secondary neurons which then cross the midline to ascend in the contralateral medial lemniscus to the thalamus. Tertiary neurons then ascend to the postcentral or sensory cortex, just as with other touch sensations. Since this wide variety of somatic leg sensation all reach the thalamus, it makes sense that the unpleasant leg sensations in patients with RLS are very diverse in character.

For patients with primary or secondary RLS, the terribly unpleasant touch sensations of RLS that often start during sleep are mapped to their leg or legs (and, much less commonly, to their arm or arms). Since most patients are not actually being subjected to bizarre touch sensations in the affected extremity, the sensations are, in effect, somatic hallucinations. That is, these sensations are perceived to originate in a limb in which no corresponding stimulus is present. For example, at the time some patients with RLS report that a leg feels as though worms are crawling in it, no worms are actually present to explain the sensations experienced. The phantom limb syndrome in amputees is a similar phenomena, where somatic sensations in the brain are mapped by the individual to a limb that is not present. They are not usually referred to as "hallucinations," but they are.

A partial explanation for the hallucinations that begin during periods of sleepiness and drowsiness or during sleep in patients with RLS may be found in the neuronal circuit that exists between the thalamus and the sensory cortex, referred to as the "thalamocortical loop."(67) Only two stable membrane potential states exist for thalamocortical neurons. During wakefulness, these neurons fire tonically which allows them to transmit information from peripheral somatic stimuli to the cortex or conscious brain (see Pathways 1-3 above). During sleep, and perhaps during times of sleepiness or drowsiness, the thalamocortical neurons enter an oscillatory state, become synchronized with the cortex, and disconnect the cortex from the outside world. When disconnected, the conscious brain gets its peripheral somatic sensory input not from peripheral somatic sensory neurons but from the thalamus and its varied inputs. The somatosensory brain is no longer looking at the external world; it is focused internally.

The primacy of sensory abnormalities in RLS—as opposed to movement abnormalities—was emphasized in a recent study published by pulmonary physicians (as opposed to sleep physicians) who noted that "The endorsement of twitching or frequent body movements in the current study was so frequent as to render it a nonspecific finding. We cannot draw any conclusions based on this reported symptom in this study, other than to suggest that asking about body twitching may not be useful in the clinical evaluation of patients."(37) The same authors noted that a consistent diagnosis of RLS could be obtained using a definition of RLS that requires " . . . uncomfortable leg sensations a few nights a week or more that are worse at night." Abnormal brain somatosensory processing in RLS patients has been described.(68)

Prior to waking, the unpleasant sensations of RLS lead to leg movements seemingly as an unconscious attempt to diminish the amplitude of the disturbing sensations. Dysfunctional leg movements and their antecedent unpleasant sensations wake the patient who then seeks relief by doing something, commonly getting out of bed and standing or walking. However, even though standing and walking diminish unpleasant limb sensations, they do so at the expense of sleep. Over half of patients with RLS report waking with symptoms 3 or more times per night on nights they experience attacks. (15) Loss of sleep is the ultimate price paid by the patients who suffer from RLS. RLS patients with severe symptoms have the least amount of sleep of any sleep disorder with the exception of sleep-loss associated with mania.(66) The sleep-loss of RLS leads to a generalized decrease in quality of life similar to other forms of insomnia, such as sleep apnea.(15, 69) RLS victims are more likely than normals to be late to work, miss work, make errors at work, and miss social events because of sleepiness.(37)

Two drugs are currently labeled by the Food and Drug Administration for the treatment of RLS: Mirapex® (pramipexole dihydrochloride), a nonergot dopamine agonist, and Requip® (ropinirole hydrochloride), a nonergot dopamine agonist. Both agents have a higher binding affinity with $D_3$ dopamine receptor subtypes than for $D_2$ for $D_4$ receptors. In two separate blinded studies of ropinirole, very large placebo affects were observed, suggesting that just the process of focusing attention on patients with RLS helps them considerably.(70,71) Off-label drug prescription for RLS is widespread. Many drugs, including iron preparations, benzodiazepines, opiates, and anticonvulsants have been used to treat RLS.(8) Some dopaminergic agents, such as the combination of levodopa/carbidopa, have caused long-term side effects which include worsening or augmentation of RLS symptoms. (9) Drugs that influence the central nervous system commonly effect more than one region of the brain, making drugs less than desirable as a first line of treatment for RLS. McCrink et al. studied 16,202 individuals, 7% of which had RLS. They documented that health-related quality of life was actually diminished in RLS patients who used prescription medications to treat RLS symptoms.(72)

As previously noted, if correction of a patient's secondary disorder or disease can correct RLS, that disorder or disease should be treated. However, most patients with RLS have no secondary disease or disorder to correct or the secondary disorder or disease is not treatable.

To relieve the unpleasant tactile sensations of RLS, patients resort to all sorts of movements and stimulations of the legs including " . . . walking about, stomping the feet, rubbing, squeezing or stroking the legs; taking hot showers or baths; or applying ointment, hot packs, or wraps to the legs."(73) As stated by Jones and Derodra, "The relief of symptoms produced by movement or rubbing may be due to the afferent sensory input effect."(25) Patients are spontaneously applying an overwhelming or swamping sensory input to serve as a "counterstimulation" to the unpleasant sensations of RLS. Once up and doing something, RLS symptoms usually subside. However, the process of getting up and walking interrupts sleep. And interrupted sleep, over the long haul, leads to decreased wakeful functioning and diminished quality-of-life.

A simple device that could provide a pleasant sensation to overwhelm or swamp the unpleasant sensations of RLS, without fully waking the patient, might be a more desirable first line treatment of RLS than drugs. Counterstimulation is a known medical therapy. To treat auditory hallucinations, personal stereo music has been applied as a counterstimulation to overwhelm or swamp auditory hallucinations.(74) Similarly, to treat a wide variety of chronic pain syndromes, transcutaneous electrical nerve stimulation has been applied as a counterstimulation to overwhelm or swamp pain.(75)

If a counterstimulus could be applied to a RLS patient at the onset of an attack while the patient were in bed, and the counterstimulus could be applied with minimal waking of the patient, sleep efficiency might be improved. As shown by FIG. 2, which illustrates a flow chart showing grades of severity of RLS and types of treatments based upon severity, adapted from Chaudhuri, many patients with mild forms for RLS spontaneously apply a counterstimuli of one sort or another to allow themselves to go back to sleep.(9)

If the RLS patient's self-treatment proves ineffective or if it requires a degree of wakefulness incompatible with a good night's sleep, then a device that applied a counterstimulus without robbing sleep might be useful.

FIG. 3 illustrates a cooling pad, embodying principles of the present invention, applied to a leg, the cooling pad applying no additional pressure than the patient sheet and mattress pad. In some patients, therapeutic counterstimulation could be as simple as making a region of the patients bedding cool, as shown in FIG. 3. Cooling that does not drop to lower than 17° C. is sensed by free nerve fibers as a cool sensation and not pain. Below 17° C., the sensation is identified by other free nerve fibers as pain.(67) (Similarly, above 42° C., heat is no longer sensed as warmth, but as pain.) If the cooling could be turned on at the onset of RLS symptoms and set to turn off as the patient fell back to sleep, a counterstimulation of a single nerve pathway might be sufficient to overwhelm the central sensations of RLS.

FIG. 4 illustrates a hard rubber ball, embodying principles of the present invention, being pressed against a patient's leg such that the skin, subcutaneous tissue, muscle, periosteum, and joints are all effected by the stimulus. In another patient, therapeutic counterstimulation might require the recruitment of a host of somatic sensory nerves to overcome the unpleasant sensations of RLS. FIG. 4 shows a ball pressed against the back of a patients leg with just enough force not to elicit pain. Free nerve endings, Merkel's disks, and Ruffini's corpuscles from the skin, Pacinian corpuscles from subcutaneous tissue, muscle spindles from the muscle, joint receptors from the knee and ankle, and Pacinian corpuscles from the interosseous membrane joining the tibia and the fibula, could all send somatic sensory signals to the brain from this stimulus. If pressure from a ball, or the like, could be applied at the onset of RLS symptoms and removed as the patient fell back to sleep, a counterstimulation from a host nerve pathways might sufficient to overwhelm the unpleasant central sensations of RLS.

A commercially available boot which diffusely applies pressure to the foot and calf has been disclosed on the world wide web (club-cleo.com/cleo-active-leggings-reflexology.html) and offered as a means of treating RLS. Similarly, a boot-like device capable of moving leg fluids to prevent deep vein thrombosis is revealed by Morgenlander in U.S. Published Patent Application Nos. 2003/0176822 A1, US 2005/0026912 A1, and US 2006/0287621 A1, in which the affected limb is subjected to " . . . positive pressure to an extremity" to effect treatment. Additionally, in U.S. Pat. No. 4,149,529, Copeland discloses an apparatus capable of applying pressure to a leg similar to Morgenlander.

REFERENCE LIST

1. Willis T: Instructions for curing the Watching evil in The London practice of physick. London: Bassett and Crooke, 1685.
2. Clark M M. Restless legs syndrome. J Am Board Fam Pract 14:368-374, 2001.
3. Ekbom K A. Restless legs: a clinical study. Acta Med Scand 158 (Supplement): 1-222, 1945.
4. Yoakum R H: Restless legs syndrome: Relief and hope for sleepless victims of a hidden epidemic. New York: Fireside, 2006.
5. Hening W, Allen R, Earley C, Kushida C, Picchietti D, Silber M. The treatment of restless legs syndrome and periodic limb movement disorder. An American Academy of Sleep Medicine Review. Sleep 22:970-999, 1999.
6. Walters A S. Towards a better definition of the restless legs syndrome. Move Disord 10:634-642, 1995.
7. Allen R P, Picchietti D, Hening W A, Trenkwalder C, Walters A S, Montplaisi J. Restless legs syndrome: diagnostic criteria, special considerations, and epidemiology. A report from the restless legs syndrome diagnosis and epidemiology workshop at the National Institutes of Health. Sleep Med 4:101-119, 2003.
8. Hening W A, Allen R P, Earley C J, Picchietti D L, Silber M H. An update on the dopaminergic treatment of restless legs syndrome and periodic limb movement disorder. Sleep 27:560-583, 2004.
9. Chaudhuri K R, Odin P, Olanow C W: Restless legs syndrome. London and New York: Taylor & Francis, 2004.
10. Phillips B, Young T, Finn L, Asher K, Hening W A, Purvis C. Epidemiology of restless legs symptoms in adults. Arch Intern Med 160:2137-2141, 2000.
11. Bjorvatn B, Leissner L, Ulfberg J, Gyring J, Karlsborg M, Regeur L, Skeidsvoll H, Nordhus I H, Pallesen S. Prevalence, severity and risk factors of restless legs syndrome in the general adult population in two Scandinavian countries. Sleep Med 6:307-312, 2005.
12. Allen R P. Controversies and challenges in defining the etiology and pathophysiology of restless legs syndrome. Am J Med 120:S13-21, 2007.
13. Cuellar N G, Strumpf N E, Ratcliffe S J. Symptoms of restless legs syndrome in older adults: outcomes on sleep quality, sleepiness, fatigue, depression, and quality of life. J Am Geriatr Soc 55:1387-1392, 2007.
14. Wolkove N, Elkholy O, Baltzan M, Palayew M. Sleep and aging: 1. Sleep disorders commonly found in older people. CMAJ 176:1299-1304, 2007.
15. Hening W, Walters A S, Allen R P, Montplaisir J, Myers A, Ferini-Strambi L. Impact, diagnosis and treatment of restless legs syndrome (RLS) in a primary care population: the REST (RLS epidemiology, symptoms, and treatment) primary care study. Sleep Med 5:237-246, 2004.
16. Allen R P, Walters A S, Montplaisir J, Hening W, Myers A, Bell T J, Ferini-Strambi L. Restless legs syndrome prevalence and impact: REST general population study. Arch Intern Med 165:1286-1292, 2005.
17. Park A, Masters C, Sayre C, Sharples T, Silver A, Stinchfield K. The year in medicine from A to Z. Time 170:??-??__, 2007.
18. Van De Vijver D A, Walley T, Petri H. Epidemiology of restless legs syndrome as diagnosed in UK primary care. Sleep Med 5:435-440, 2004.
19. Trenkwalder C. Restless-legs syndrome in primary care: counting patients in Idaho. Lancet Neurol 3:83, 2004.
20. Nichols D A, Allen R P, Grauke J H, Brown J B, Rice M L, Hyde P R, Dement W C, Kushida C A. Restless legs syndrome symptoms in primary care: a prevalence study. Arch Intern Med 163:2323-2329, 2003.
21. Hanson M, Honour M, Singleton A, Crawley A, Singleton A, Hardy J, Gwinn-Hardy K. Analysis of familial and sporadic restless legs syndrome in age of onset, gender, and severity features. J Neurol 251:1398-1401, 2004.
22. Ziaei J, Saadatnia M. Epidemiology of familial and sporadic restless legs syndrome in Iran. Arch Iran Med 9:65-67, 2006.
23. Mata I F, Bodkin C L, Adler C H, Lin S C, Uitti R J, Farrer M J, Wszolek Z K. Genetics of restless legs syndrome. Parkinsonism Relat Disord 12:1-7, 2006.
24. Kemlink D, Polo O, Montagna P, Provini F, Stiasny-Kolster K, Oertel W, de Weerd A, Nevsimalova S, Sonka K, Hogl B, Frauscher B, Poewe W, Trenkwalder C, Pramstaller P P, Ferini-Strambi L, Zucconi M, Konofal E, Arnulf I, Hadjigeorgiou G M, Happe S, Klein C, Hiller A, Lichtner P, Meitinger T, Muller-Myshok B, Winkelmann J. Family-based association study of the restless legs syndrome loci 2 and 3 in a European population. Mov Disord 22:207-212, 2007.
25. Jones H J, Derodra J K. Restless legs syndrome—a review. Eur J Vasc Endovasc Surg 14:430-432, 1997.
26. Evidente V G, Adler C H. How to help patients with restless legs syndrome. Discerning the indescribable and relaxing the restless. Postgrad Med 105:59-61, 65-66, 73-74, 1999.
27. Lee K A, Zaffke M E, Baratte-Beebe K. Restless legs syndrome and sleep disturbance during pregnancy: the role of folate and iron. J Womens Health Gend Based Med 10:335-341, 2001.
28. Ulfberg J, Nystrom B, Carter N, Edling C. Prevalence of restless legs syndrome among men aged 18 to 64 years: an association with somatic disease and neuropsychiatric symptoms. Mov Disord 16:1159-1163, 2001.
29. Ondo W. Epidemiology of restless legs syndrome. Sleep Med 3 Suppl:S13-15, 2002.
30. Ohayon M M, Roth T. Prevalence of restless legs syndrome and periodic limb movement disorder in the general population. J Psychosom Res 53:547-554, 2002.
31. Tan E K, Ho S C, Eng P, Loh L M, Koh L, Lum S Y, Teoh M L, Yih Y, Khoo D. Restless legs symptoms in thyroid disorders. Parkinsonism Relat Disord 10:149-151, 2004.
32. Ulfberg J, Nystrom B. Restless legs syndrome in blood donors. Sleep Med 5:115-118, 2004.
33. Lopes L A, Lins Cde M, Adeodato V G, Quental D P, de Bruin P F, Montenegro R M Jr, de Bruin V M. Restless legs syndrome and quality of sleep in type 2 diabetes. Diabetes Care 28:2633-2636, 2005.
34. Lakshminarayanan S, Paramasivan K D, Walters A S, Wagner M L, Patel S, Passi V. Clinically significant but unsuspected restless legs syndrome in patients with sleep apnea. Mov Disord 20:501-503, 2005.
35. O'Keeffe S T. Secondary causes of restless legs syndrome in older people. Age Aging 34:349-352, 2005.
36. Garcia-Borreguero D, Egatz R, Winkelmann J, Berger K. Epidemiology of restless legs syndrome: the current status. Sleep Med Rev 10:153-167, 2006.
37. Phillips B, Hening W, Britz P, Mannino D. Prevalence and correlates of restless legs syndrome: results from the 2005 National Sleep Foundation Poll. Chest 129:76-80, 2006.
38. Pearson V E, Allen R P, Dean T, Gamaldo C E, Lesage S R, Earley C J. Cognitive deficits associated with restless legs syndrome (RLS). Sleep Med 7:25-30, 2006.
39. Chahine L M, Chemali Z N. Restless legs syndrome: a review. CNS Spectr 11:511-520, 2006.
40. Merlino G, Fratticci L, Valente M, Del Giudice A, Noacco C, Dolso P, Cancelli I, Scalise A, Gigli G L. Association of restless legs syndrome in type 2 diabetes: a case-control study. Sleep 30:866-871, 2007.
41. Merlino G, Valente M, Serafini A, Gigli G L. Restless legs syndrome: diagnosis, epidemiology, classification and consequences. Neurol Sci 28 Suppl 1:S37-46, 2007.
42. Aigner M, Prause W, Freidl M, Weiss M, Izadi S, Bach M, Saletu B. High prevalence of restless legs syndrome in somatoform pain disorder. Eur Arch Psychiatry Clin Neurosci 257:54-57, 2007.
43. Gomez-Choco M J, Iranzo A, Blanco Y, Graus F, Santamaria J, Saiz A. Prevalence of restless legs syndrome and REM sleep behavior disorder in multiple sclerosis. Mult Scler 13:805-808, 2007.
44. Manconi M, Fabbrini M, Bonanni E, Filippi M, Rocca M, Murri L, Ferini-Strambi L. High prevalence of restless legs syndrome in multiple sclerosis. Eur J Neurol 14:534-539, 2007.
45. Ramchandren S, Chervin R D. The relationship between restless legs syndrome and neuropathy. Mov Disord 22:588; author reply 589, 2007.
46. Berger K, Luedemann J, Trenkwalder C, John U, Kessler C. Sex and the risk of restless legs syndrome in the general population. Arch Intern Med 164:196-202, 2004.
47. Hogl B, Kiechl S, Willeit J, Saletu M, Frauscher B, Seppi K, Muller J, Rungger G, Gasperi A, Wenning G, Poewe W. Restless legs syndrome: a community-based study of prevalence, severity, and risk factors. Neurology 64:1920-1924, 2005.
48. Winkelmann J, Stautner A, Samtleben W, Trenkwalder C. Long-term course of restless legs syndrome in dialysis patients after kidney transplantation. Mov Disord 17:1072-1076, 2002.
49. Mucsi I, Molnar M Z, Ambrus C, Szeifert L, Kovacs A Z, Zoller R, Barotfi S, Remport A, Novak M. Restless legs syndrome, insomnia and quality of life in patients on maintenance dialysis. Nephrol Dial Transplant 20:571-577, 2005.
50. Moline M L, Broch L, Zak R. Sleep in women across the life cycle from adulthood through menopause. Med Clin North Am 88:705-736, ix, 2004.
51. Manconi M, Govoni V, De Vito A, Economou N T, Cesnik E, Casetta I, Mollica G, Ferini-Strambi L, Granieri E. Restless legs syndrome and pregnancy. Neurology 63:1065-1069, 2004.
52. Bucher S F, Seelos K C, Oertel W H, Reiser M, Trenkwalder C. Cerebral generators involved in the pathogenesis of the restless legs syndrome. Ann Neurol 41:639-645, 1997.
53. Goodman J D, Brodie C, Ayida G A. Restless leg syndrome in pregnancy. BMJ 297:1101-1102, 1988.
54. Rangarajan S, D'Souza G A. Restless legs syndrome in Indian patients having iron deficiency anemia in a tertiary care hospital. Sleep Med 8:247-251, 2007.
55. Earley C J, B Barker P, Horska A, Allen R P. MRI-determined regional brain iron concentrations in early- and late-onset restless legs syndrome. Sleep Med 7:458-461, 2006.
56. Mizuno S, Mihara T, Miyaoka T, Inagaki T, Horiguchi J. CSF iron, ferritin and transferrin levels in restless legs syndrome. J Sleep Res 14:43-47, 2005.
57. Ondo W, Jankovic J. Restless legs syndrome: clinicoetiologic correlates. Neurology 47:1435-1441, 1996.
58. Walters A S, Wagner M, Hening W A. Periodic limb movements as the initial manifestation of restless legs syndrome triggered by lumbosacral radiculopathy. Sleep 19:825-826, 1996.
59. Gemignani F, Marbini A. Restless legs syndrome and peripheral neuropathy. J Neurol Neurosurg Psychiatry 72:555, 2002.
60. Gemignani F, Brindani F, Negrotti A, Vitetta F, Alfieri S, Marbini A. Restless legs syndrome and polyneuropathy. Mov Disord 21:1254-1257, 2006.
61. Kanter A H. The effect of sclerotherapy on restless legs syndrome. Dermatol Surg 21:328-332, 1995.
62. Symonds C P. Nocturnal myoclonus. J Neurol Neurosurg Psychiatry 16:166-171, 1953.
63. Lugaresi E, Coccagna G, Tassinari C A, Ambrosetto C. [Polygraphic data on motor phenomena in the restless legs syndrome]. Riv Neurol 35:550-561, 1965.
64. Montplaisir J, Boucher S, Poirier G, Lavigne G, Lapierre O, Lesperance P. Clinical, polysomnographic, and genetic characteristics of restless legs syndrome: a study of 133 patients diagnosed with new standard criteria. Mov Disord 12:61-65, 1997.

65. Zucconi M, Ferini-Strambi L. Epidemiology and clinical findings of restless legs syndrome. Sleep Med 5:293-299, 2004.
66. Allen R P, Earley C J. Restless legs syndrome: a review of clinical and pathophysiologic features. J Clin Neurophysiol 18:128-147, 2001.
67. Purves D, Augustine G J, Fitzpatrick D, Hall W C, LaMantia A-S, McNamara J O, White L E: Neuroscience: Fourth Edition. Sunderland, M A: Sinauer Associates, Inc., 2008.
68. Schattschneider J, Bode A, Wasner G, Binder A, Deuschl G, Baron R. Idiopathic restless legs syndrome: abnormalities in central somatosensory processing. J Neurol 251: 977-982, 2004.
69. Winkelman J W, Finn L, Young T. Prevalence and correlates of restless legs syndrome symptoms in the Wisconsin Sleep Cohort. Sleep Med 7:545-552, 2006.
70. Walters A S, Ondo W G, Dreykluft T, Grunstein R, Lee D, Sethi K. Ropinirole is effective in the treatment of restless legs syndrome. TREAT RLS 2: a 12-week, double-blind, randomized, parallel-group, placebo-controlled study. Mov Disord 19:1414-1423, 2004.
71. Trenkwalder C, Garcia-Borreguero D, Montagna P, Lainey E, de Weerd A W, Tidswell P, Saletu-Zyhlarz G, Telstad W, Ferini-Strambi L. Ropinirole in the treatment of restless legs syndrome: results from the TREAT RLS 1 study, a 12 week, randomised, placebo controlled study in 10 European countries. J Neurol Neurosurg Psychiatry 75:92-97, 2004.
72. McCrink L, Allen R P, Wolowacz S, Sherrill B, Connolly M, Kirsch J. Predictors of health-related quality of life in sufferers with restless legs syndrome: a multi-national study. Sleep Med 8:73-83, 2007.
73. Mahowald M W. Restless legs syndrome: the CNS/iron connection. J Lab Clin Med 147:56-57, 2006.
74. Johnston O, Gallagher A G, McMahon P J, King D J. The efficacy of using a personal stereo to treat auditory hallucinations. Preliminary findings. Behav Modif 26:537-549, 2002.
75. Chabal C, Fishbain D A, Weaver M, Heine L W. Long-term transcutaneous electrical nerve stimulation (TENS) use: impact on medication utilization and physical therapy costs. Clin J Pain 14:66-73, 1998.

SUMMARY

According to a first aspect of the invention, a system for generating a counter-stimulation in a patient suffering from RLS comprises a device configured and arranged to generate a counter-stimulation in a patient suffering from RLS, the counter-stimulation of an amplitude, intensity, and time duration lower than that which would wake the patient and higher than that sufficient to relieve RLS, or sufficient to relieve RLS symptoms and allow the patient to return to sleep, a controller configured and arranged to drive the counter-stimulation generation device, the controller in communication with the counter-stimulation device, and a base configured and arranged to hold the counter-stimulation generation device adjacent to a patient, the counter-stimulation device attached to the base.

According to another aspect of the present invention, a method of treating RLS comprises selecting a patient experiencing RLS, and stimulating a portion of the patient at an amplitude, intensity, and duration sufficient to act as a counter-stimulation to RLS.

Still other aspects, features, and attendant advantages of the present invention will become apparent to those skilled in the art from a reading of the following detailed description of embodiments constructed in accordance therewith, taken in conjunction with the accompanying drawings.

BRIEF DESCRIPTION OF THE DRAWINGS

The invention of the present application will now be described in more detail with reference to exemplary embodiments of the apparatus and method, given only by way of example, and with reference to the accompanying drawings, in which:

FIGS. 39 and 40 illustrate cross-sectional views, taken a line A-A in FIG. 10, showing several features of other embodiments of the invention;

FIG. 41 illustrates a side elevational view of an embodiment of a device in accordance with the present invention, under a patient's legs;

FIGS. 42 and 43 illustrate cross-sectional views, taken a line A-A in FIG. 10, showing several features of other embodiments of the invention;

FIG. 44 illustrates a side elevational view of an embodiment of a device in accordance with the present invention, under a patient's legs;

FIG. 56 illustrates another embodiment of a device for RLS counter-stimulation;

FIG. 57 illustrates a cross-sectional view, taken at line B-B in FIG. 56;

FIG. 60 illustrates yet another embodiment of a device for RLS counter-stimulation;

FIGS. 71-73 illustrate another embodiment of a device useful for producing mechanical vibrations for RLS counter-stimulation.

DETAILED DESCRIPTION OF EXEMPLARY EMBODIMENTS

Figure 1:
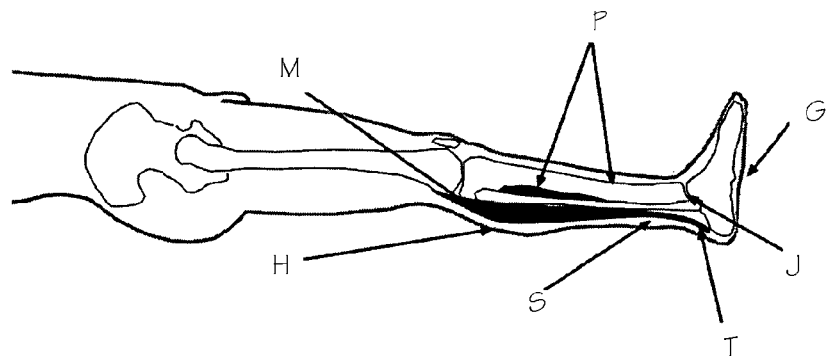
FIG. 1 illustrates a human leg including anatomical features.
Figure 3:
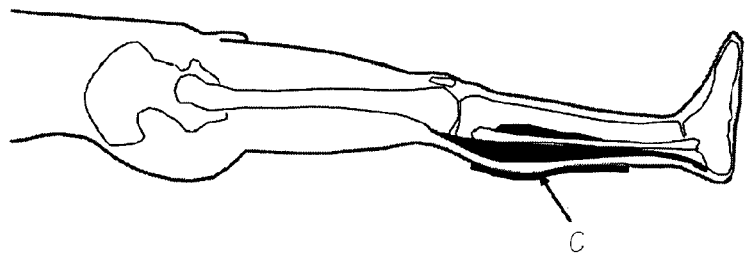
FIG. 3 illustrates a human leg and the calf thereof.
Figure 4:
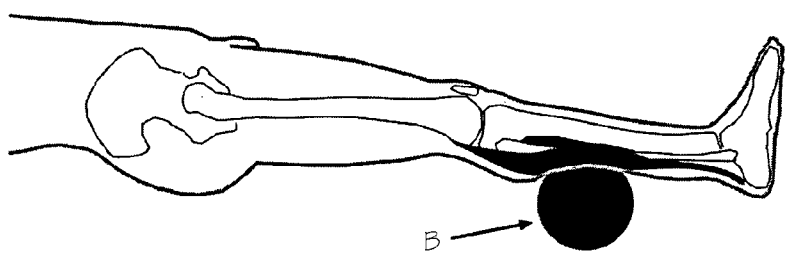
FIG. 4 illustrates a human leg with the calf thereof resting on a ball.

Referring to the drawing figures, like reference numerals designate identical or corresponding elements throughout the several figures.

It is believed that that most people in the RLS-suffering population are undiagnosed or symptoms are not sufficient to seek treatment. Most of those that do seek treatment are adequately treated by teaching improved sleep hygiene. A few patients may only be amenable to treatment by dopamine, as the symptoms are so severe that counter stimulation of the patient does not relieve or prevent the symptoms. Thus, those falling in a middle group, who do not benefit from sleep hygiene training and for which neuro-active drugs are an extreme treatment, can particularly benefit from additional therapeutic options.

TABLE 1 top level RLS treatment matrix

| RLS symptoms | Mild Symptoms | Mild to Severe | Severe |
| --- | --- | --- | --- |
| Patient experience | May be undiagnosed and untreated. | Sleep is occasionally interrupted and patient seeks medical attention | Sleep is nearly continuously interrupted |
| Treatment required | Sleep hygiene may be sufficient therapy | Counter stimulation to prevent the sensory seizure provides adequate relief | Pharmacologic treatment after failure of lesser therapies |

Figure 2:
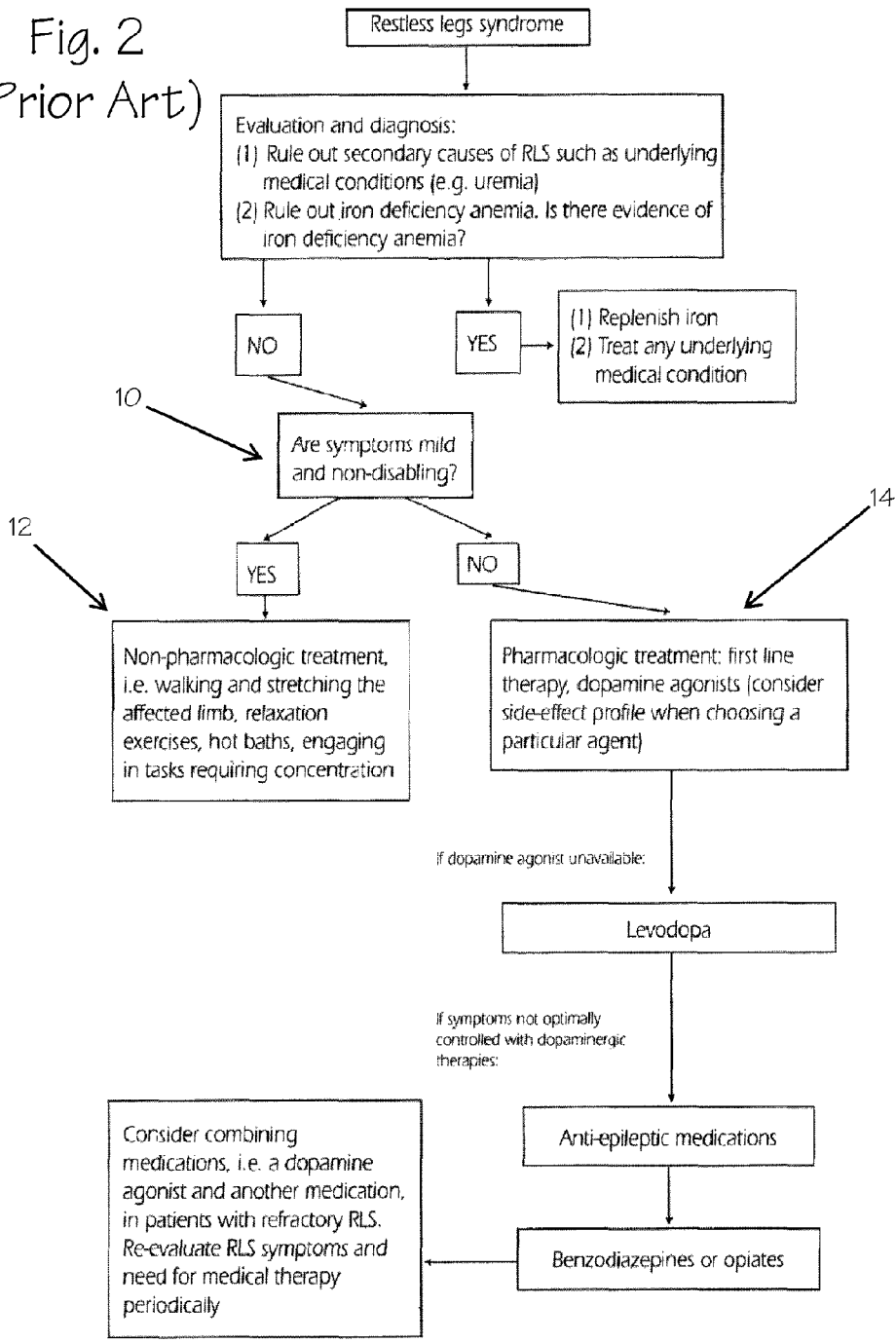
FIG. 2 illustrates a decision flow chart relating to the treatment of RLS.

Referring back to FIG. 2, an exemplary process of diagnosing and treating RLS is illustrated. With reference to Table 1 and FIG. 2, the determination that an RLS-sufferer has mild symptoms, 10, indicates that sleep hygiene may be sufficient therapy for the patient. When a determination is made that the patient's RLS is severe, 14, then other treatment options, such as pharmacologic treatment after the failure of lesser therapies, is indicated. In between, when a determination has been made that the patient's RLS is, thus, mild to severe, 12, counter-stimulation, to prevent the sensory seizure, can provide adequate relief to the patient, and is indicated. Particularly advantageous, however, are aspects of the present invention in which the counter stimulation of the patient is conducted within a stimulation window, with a level of stimulation high enough that it acts to counter the 'hallucination' discussed above, while being below a level which will awaken the patient.

Figure 5:
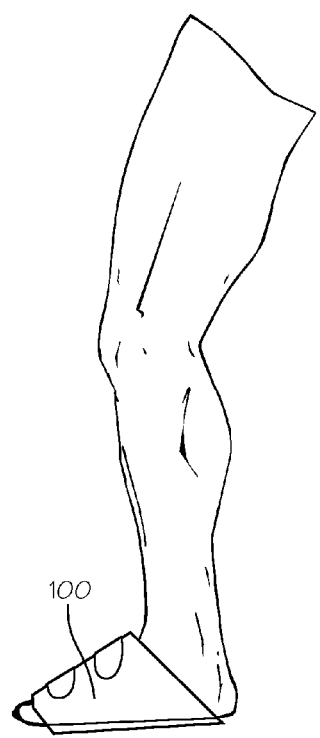
FIG. 5 illustrates a human leg with a RLS counter-stimulation device embodying principles of the present invention positioned on the foot.
Figure 6:
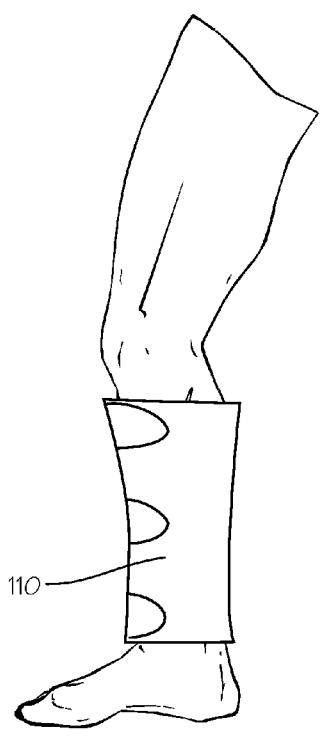
FIG. 6 illustrates a human leg with a RLS counter-stimulation device embodying principles of the present invention positioned on the calf.
Figure 7:
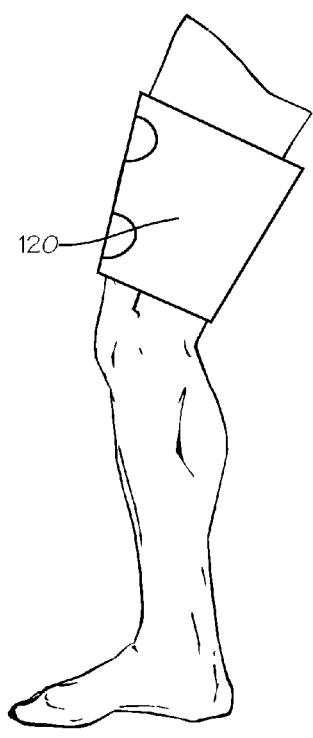
FIG. 7 illustrates a human leg with a RLS counter-stimulation device embodying principles of the present invention positioned on the thigh.

Turning now to FIG. 5, an exemplary embodiment of a device 100 is illustrated by which stimulation can be applied to the patient's foot only, but can be applied to the bottom, top, side, or any combination thereof. With reference to FIG. 6, another exemplary embodiment of a device 110 is illustrated by which stimulation can be applied to the patient's calf only, to the shin, or in combination. With reference to FIG. 7, yet another exemplary embodiment of a device 120 is illustrated by which stimulation can be effected to the patient's thigh only, by applying stimulation to the front, back, side, or in any combination thereof.

Figures 8, 9:
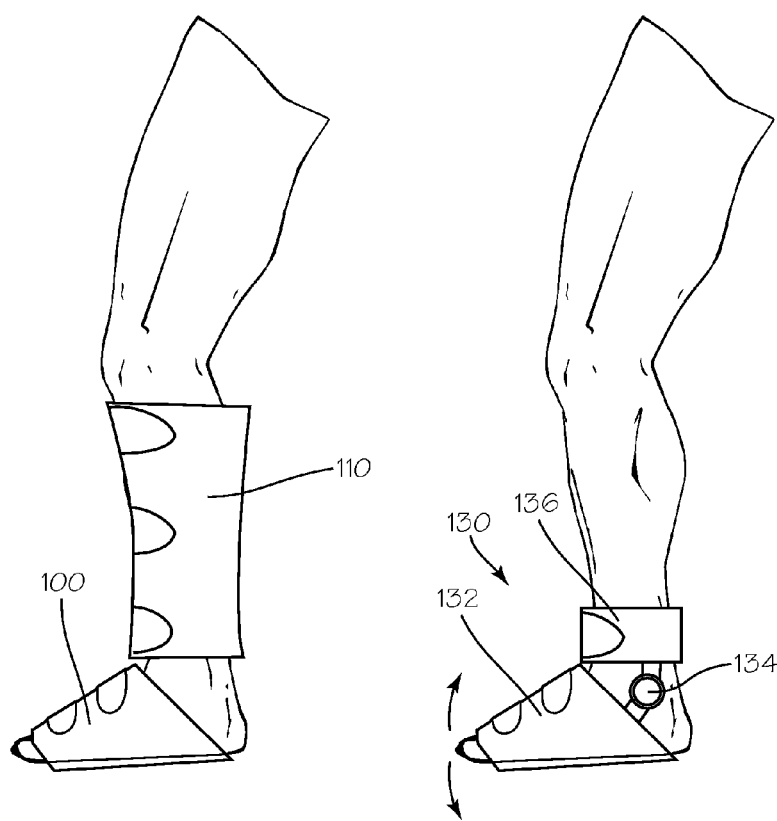
FIG. 8 illustrates a human leg with a RLS counter-stimulation device embodying principles of the present invention positioned on the foot and calf.
FIG. 9 illustrates a human leg with a RLS counter-stimulation device embodying principles of the present invention positioned on the foot and ankle.
Figure 10:
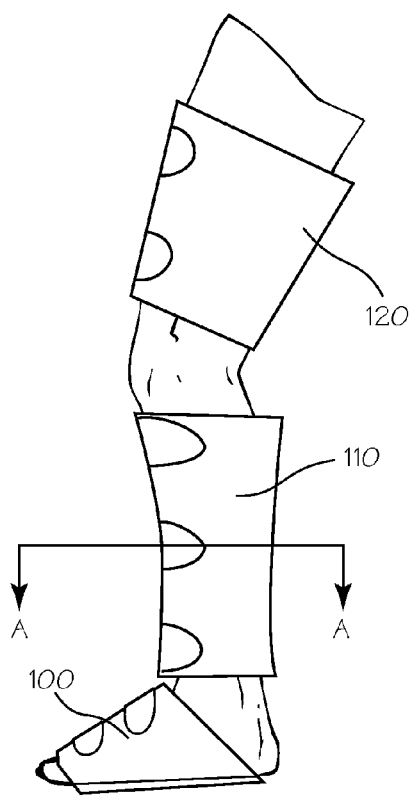
FIG. 10 illustrates a human leg with a RLS counter-stimulation device embodying principles of the present invention positioned on the foot, calf, and thigh.
Figure 11:
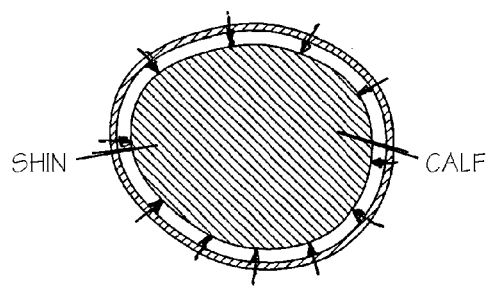
FIGS. 11-14 illustrate cross-sectional views, taken a line A-A in FIG. 10, showing several features of embodiments of the invention.
Figure 12:
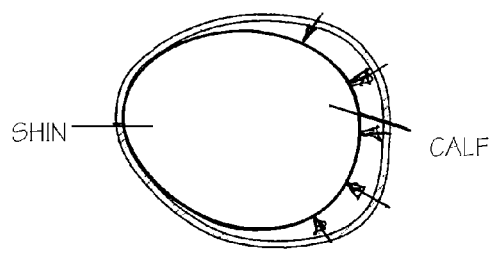

For example, combined stimulation can be applied to the patient's foot and calf, as illustrated in FIG. 8, either in a stimulation sequence or in unison. With reference to FIG. 9, the counter-stimulation can take the form of the application of motion to part of the patient's body, e.g., a torsion device 130 can be used to flex the patient's ankle, which may flex unilaterally or bilaterally. In this exemplary device 130, the device is driven to produce the flexing of muscles and the sensation of motion to the patient's brain. The exemplary device 130 can include a portion 132 which, similar to the device 100, is shoe-shaped so that it follows the contours of the patient's foot, a hinge or pivot 134 to which the shoe-shaped portion 132, and an ankle cuff 136 also attached to the pivot. Not illustrated in FIG. 9 is a motor, linear actuator, or the like which is connected to the shoe-shaped portion 132 and selectively moves the portion 132 relative to the patient's calf. With reference to FIG. 10, an embodiment is illustrated which exemplifies a combined counter-stimulation, in which stimulation of all three areas (foot, lower leg, thigh) simultaneously, or any two in combination, is utilized. FIG. 11, which illustrates a cross-sectional view at line A-A in FIG. 10, illustrates that the stimulation can be performed around the full circumference of the thigh or lower leg; FIG. 12, which also illustrates a cross-sectional view at line A-A in FIG. 10, illustrates how stimulation can performed over only a portion of the circumference of the thigh or lower leg; the invention is not limited to application of counter-stimulation to the calf, as the illustration of FIG. 12 is merely exemplary.

Figure 13:
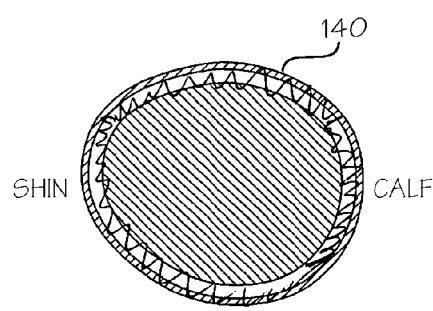
Figure 14:
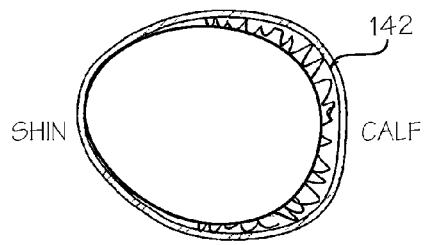

FIGS. 13 and 14 illustrate exemplary embodiments, in which circumferential pressure is applied to a portion of the patient's body. In an exemplary embodiment illustrated in FIG. 13, a circumferential bladder 140, which can be pneumatic or hydraulic, applies low pressure to the patient to stimulate, but not at a level sufficient to pump blood, as in venous boots; 3-20 mm Hg of pressure is preferred. With reference to FIG. 14, a semi-circumferential bladder 142 applies lower pressure to stimulate the patient, but not pump blood, and similarly 3-20 mm Hg of pressure can provide counter-stimulation. Not illustrated is a fluid pump and controller connected to the bladder 140, 142, which supplies fluid at pressure to the bladders so that the bladder can stimulate.

Figure 15:
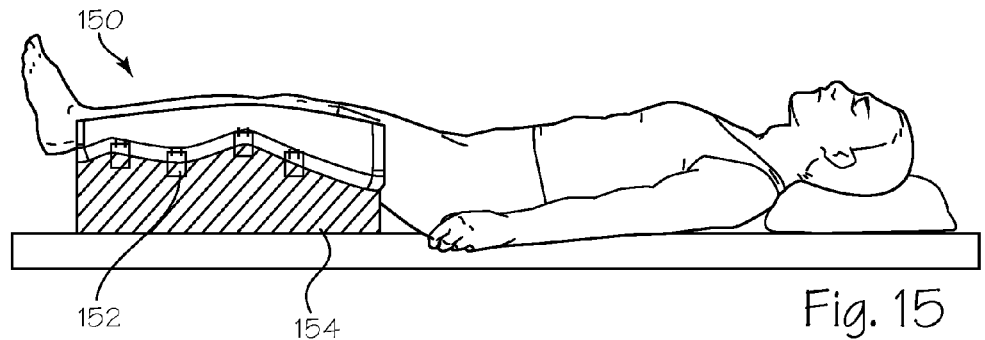
FIG. 15 illustrates a side elevational view of an embodiment of a device in accordance with the present invention, under a patient's legs.
Figure 16:
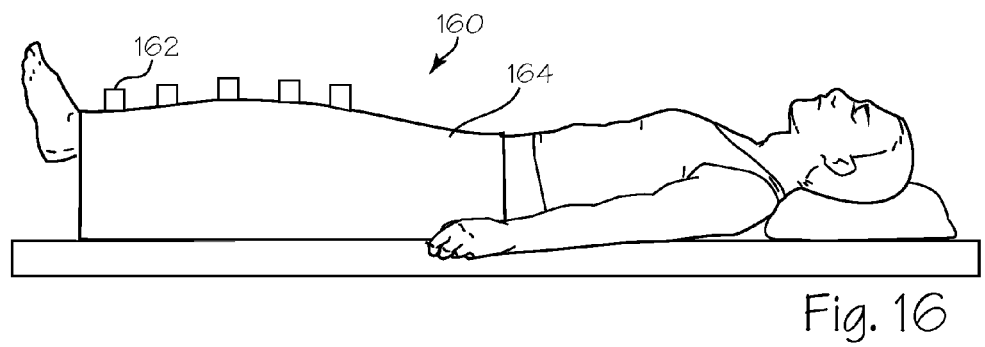
FIG. 16 illustrates a side elevational view of an embodiment of a device in accordance with the present invention, over a patient's legs.

Further embodiments embodying principles of the invention involve the application of mechanical point pressure to the patient as a counter stimulation to RLS. With reference to FIG. 15, an exemplary device 150 includes a single (or array of) pneumatic cylinders, electric solenoids, inflatable balloons, or similar mechanical point pressure applicators 152 which can be used to apply a controlled counter-stimulation to a portion of the patient's body, here the bottoms of the patient's legs being illustrated by example; a pillow block 154 can optionally be provided for comfort, elevation, and to house the mechanisms and controls which activate the point pressure applicators. Similarly, with reference to FIG. 16, an exemplary device 160 includes a single (or array of) pneumatic cylinders, electric solenoids, inflatable balloons, or similar mechanical point pressure applicators 162 which can be used to apply a controlled counter-stimulation to a top portion of the patient's body; a blanket or pad 164 can optionally be draped over the patient's legs for comfort, and to mount the devices.

Figure 17:
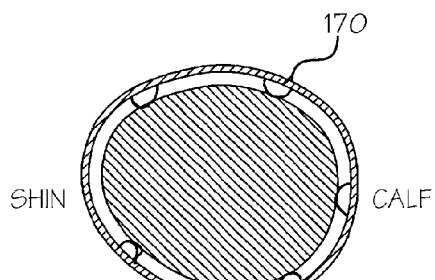
FIGS. 17 and 18 illustrate cross-sectional views, taken a line A-A in FIG. 10, showing several features of other embodiments of the invention.
Figure 18:
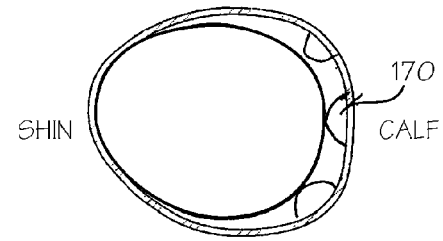

For embodiments employing pneumatic point pressure application, with reference to FIGS. 17 and 18, one or more inflatable balloons 170 can be used for local pressure stimulation. Advantageously a cuff is not used, because a cuff is prone to cause blood movement, a treatment associated with venous disorders, which is too strong of a counter-stimulation for most patients to not be awoken. The focal pressure applied to the patient, according to principles of the invention, is sufficient to provide sensory input, but not so much as to move blood in the patient's venous systems and particularly advantageously does not wake the patient.

Figure 19:
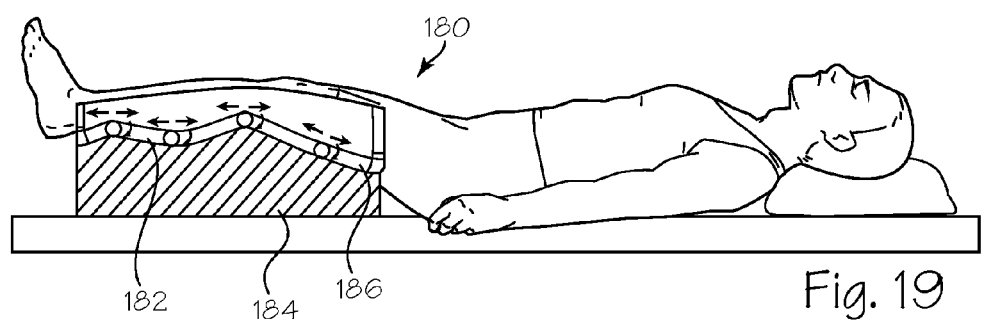
FIG. 19 illustrates a side elevational view of an embodiment of a device in accordance with the present invention, under a patient's legs.

FIG. 19 illustrates a system 180 embodying principles of the invention, in which mechanical touch is utilized to produce counter-stimulation. By way of a non-limiting example, rollers 182 are provided which spin on their axes and may optionally track along the patient's leg, optionally housed within a pillow block 184 as discussed above. The roller itself optionally is formed of or covered with a soft foam which drags on the patient's skin, or hard rubber. The rollers may be fixed in position and rotate, causing friction, or, alternately, the rollers may be on a track 186 and move along the patient as they rotate, rolling over the patient's skin to stimulate an area.

Figure 20:
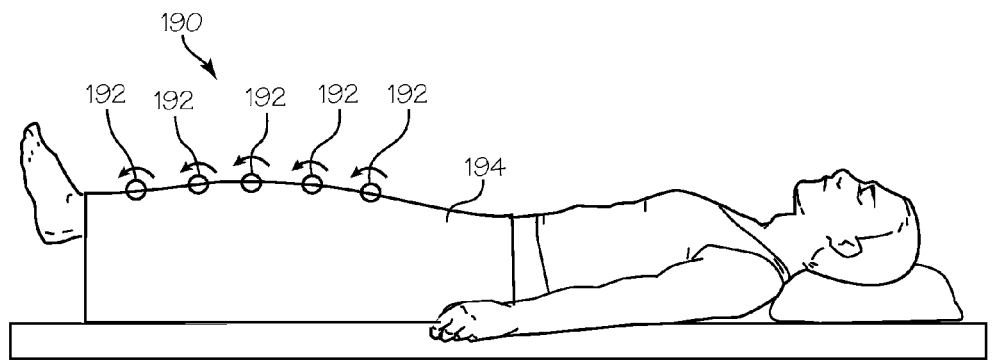
FIG. 20 illustrates a side elevational view of an embodiment of a device in accordance with the present invention, over a patient's legs.

With reference to FIG. 20, yet another embodiment 190, complying with principles of the invention, also relies on the mechanical-touch principle to provide counter-stimulation to RLS. Soft or hard rollers 192 are used to drag or "roll" on the patient's skin, in a manner similar to the rollers described with reference to FIG. 19. A blanket or pad 194 can be provided on top of the patient's legs, both for comfort and to mount the devices.

Figure 21:
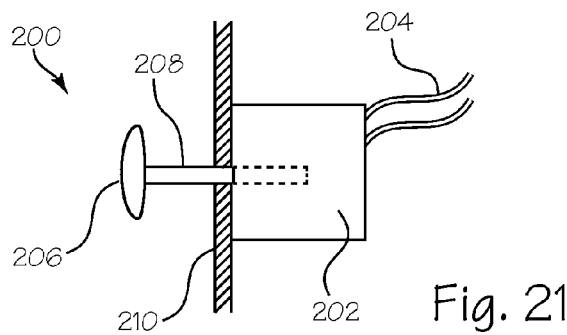
FIG. 21 schematically illustrates an exemplary device for producing counter-stimulation by pressure application.
Figure 22:
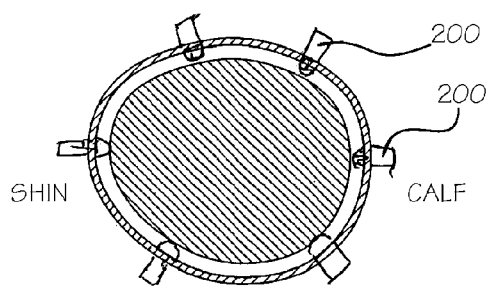
FIGS. 22-25 illustrate cross-sectional views, taken a line A-A in FIG. 10, showing several features of other embodiments of the invention.
Figure 23:
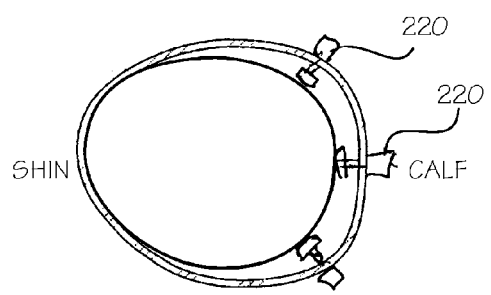

With reference to FIGS. 21-23, electromechanical or pneumatic cylinders 200 embodying principles of the invention are illustrated for providing counter-stimulation to RLS. An electrical solenoid 202 can be positioned to provide local pressure stimulation, and can be electrically powered, e.g., 12/24 VDC or 120 VAC, as at 204, to provide a pressure timing mechanism to control an "on" pressure cycle and an "off" rest cycle. The pressure can be adjusted to drive the voltage applied to the solenoid. Additionally, the maximum and minimal travel distances of the pad/rod 208, and frequency, can be made variable. The cylinder or cylinders 200 can be mounted to a wrap or other support 210, similar to such structures described elsewhere herein, with the pressure pad 206 directed toward the patient.

With reference to FIG. 23, air pressure can be supplied to provide hydraulic pressure on a "pancake" cylinder 220 to minimize the profile of the device. A controller (not illustrated) is provided to increase pressure to create more force on the cylinder rod, decrease pressure to reduce the force on cylinder rod, can ramp or the fluctuate pressure to create a "massage", and/or can adjust the frequency and/or amplitude to make the stimulation more vibratory.

Figures 24, 25:
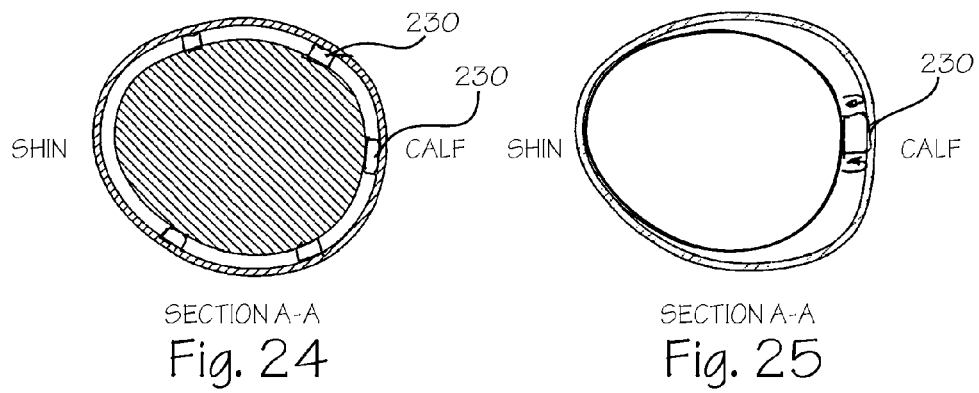

With reference to FIGS. 24 and 25, which are illustrations of cross-sectional views similar to prior figures, a touch and roll embodiment is illustrated. As illustrated in FIG. 24, circumferentially-applied counter-stimulation utilizes powered rollers 230, which may be solid or foam, and which drag on the skin or roll along the skin. Optionally, the surfaces of the rollers can be provided with an extra texture, e.g., dimples, for additional sensation. With reference to FIG. 25, localized transmission of a counter-stimulation for treating RLS can be applied by a powered roller, e.g., on one side of the foot, lower leg, or thigh, which likewise drags on the skin or rolls along the skin.

Figure 26:
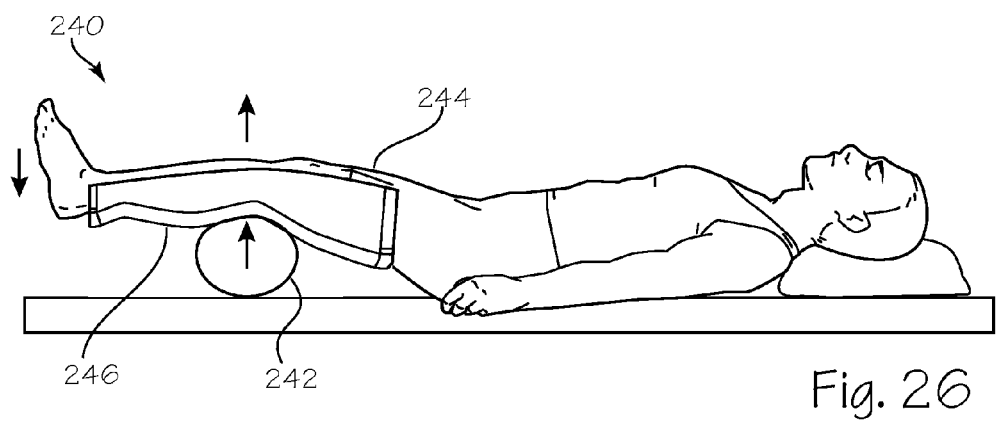
FIGS. 26-28 illustrate side elevational views of embodiments of a device in accordance with the present invention, under a patient's legs.
Figure 27:
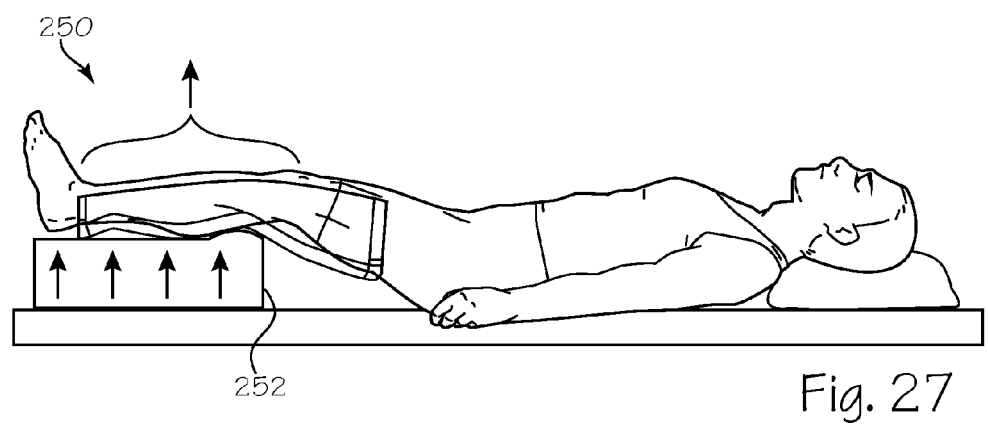
Figure 28:
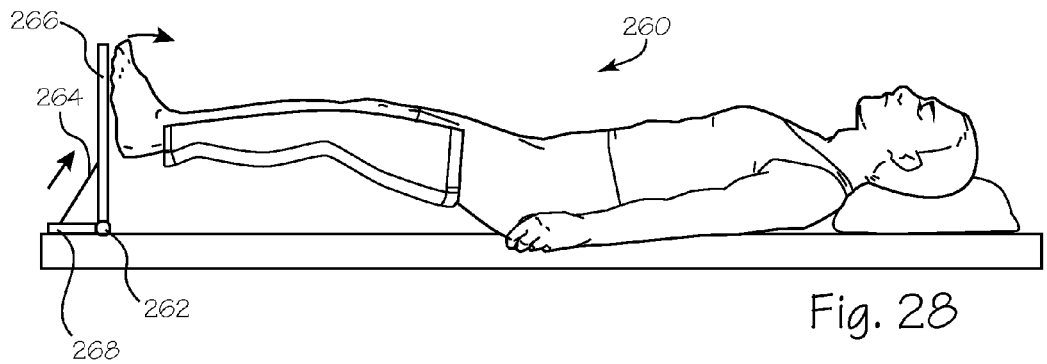

According to yet further principles of the invention, counter-stimulation for treatment of RLS can be produced by stretching the patient's muscle(s). With reference to an exemplary embodiment illustrated in FIG. 26, a device 240 is provided, such as an air bladder, pneumatic cylinder, or a simple mechanical lift 242, which causes the thigh muscles 244 to flex as the patient's knee is lifted. Similarly, the calf 246 is flexed as the patient's knee is lifted. The flexion of either or both of these muscles provides a counter-stimulation to RLS. With reference to FIG. 27, an exemplary device includes an air bladder or pneumatic cylinder 252 which can be positioned under the lower legs and feet of the patient; movement up causes the thigh muscles to flex and stretch, thus providing a counter-stimulation. With reference to FIG. 28, a footboard 260 is provided which, upon actuation of an appropriate mechanism to push the upstanding portion 266 of the footboard, flexes and stretches the patient's calf muscles, providing a counter-stimulation to RLS. By way of non-limiting example, the footboard 260 can include a relatively stationary platform 268 and a force transmission member 264 connecting the platform to the upstanding portion 266 at a pivot 262; moving the member 264, e.g., by motor or the like (not illustrated) moves the portion 266 and flexes the patient's foot, causing a counter-stimulation.

Figure 29:
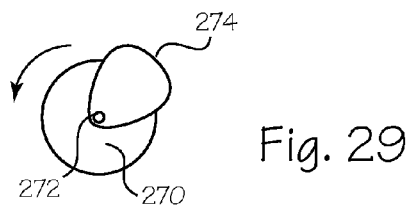
FIG. 29 schematically illustrates an embodiment of a device which mechanically produces vibration counter-stimulation.
Figure 30A:
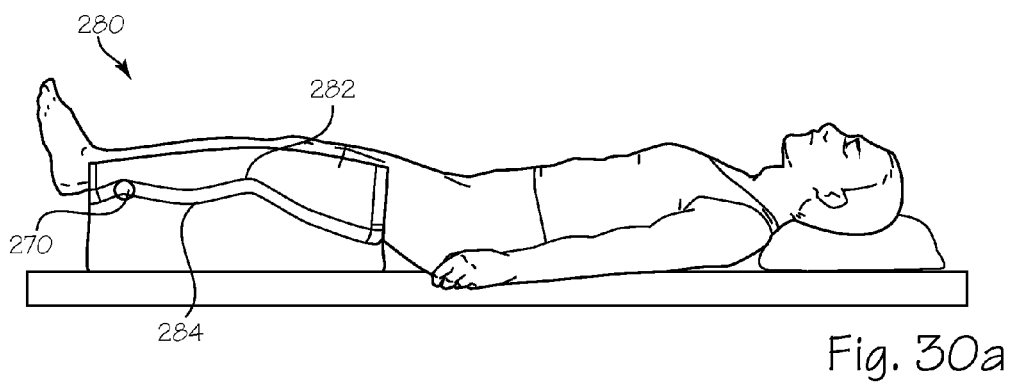
FIG. 30a illustrates a side elevational view of an embodiment of a device in accordance with the present invention, under a patient's legs.
Figure 30B:
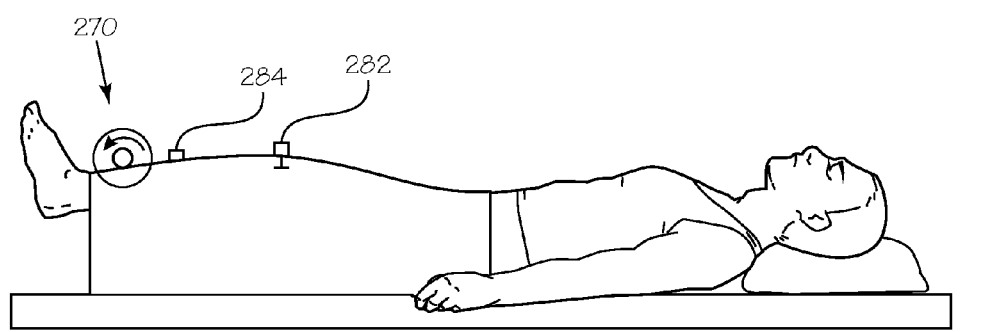
FIG. 30b illustrates a side elevational view of an embodiment of a device in accordance with the present invention, over a patient's legs.

According to yet further principles of the invention, counter-stimulation for treatment of RLS can be produced by mechanical vibration. With reference to an exemplary embodiment illustrated in FIG. 29, an electrical motor 270 provided with an eccentric weight 274 mounted to the motor shaft 272 can be provided which, upon actuation, rotates the weight and thus vibrates either a local region of the patient's body or, e.g., the entire leg of the patient to create a counter-stimulation to RLS. Another exemplary embodiment includes a pneumatic cylinder or electric solenoid which is driven to cause such a vibration, or a piezo-electric vibrator or speaker. With reference to FIGS. 30a and 30b, the mechanical vibratory device(s) 270 can be positioned on top of the patient (FIG. 30b), as with other embodiments described herein, with one or more electrical motors provided with an eccentric weight, pneumatic cylinder or electric solenoid 282, and/or a piezo-electric vibrator or speaker 284.

Figures 31, 32:
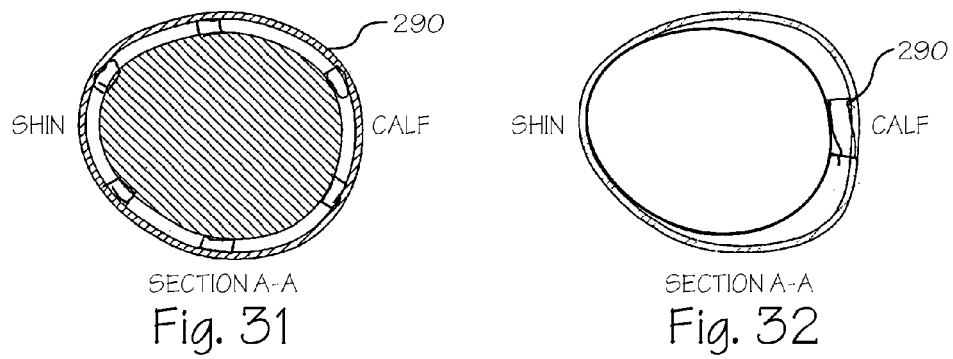
FIGS. 31 and 32 illustrate cross-sectional views, taken a line A-A in FIG. 10, showing several features of other embodiments of the invention.

With respect to using vibration as a counter-stimulation for RLS, the vibration can be provided with variable frequency and amplitude, from 1 cycle/minute to 1000 cycles/second. By way of non-limiting example, numerous devices can be utilized to create the vibration, including, but not limited to, a piezo-chip, a loudspeaker, a motor with eccentric weight, an electrical solenoid; and can be electrically driven (120 VAC, 12 VDC, 24 DC battery powered, rechargeable, etc.), and/or can be driven by a pneumatic cylinder. As illustrated in FIG. 31, a series of vibrators 290 can be provided which wrap around the patient's leg or be applied to the leg, and can be turned on, run for a predetermined period of time, and turned off after a specified time. FIG. 32 illustrates an exemplary embodiment in which the vibrator 290 is localized, rather than being provided as a series of vibrators.

Figure 33:
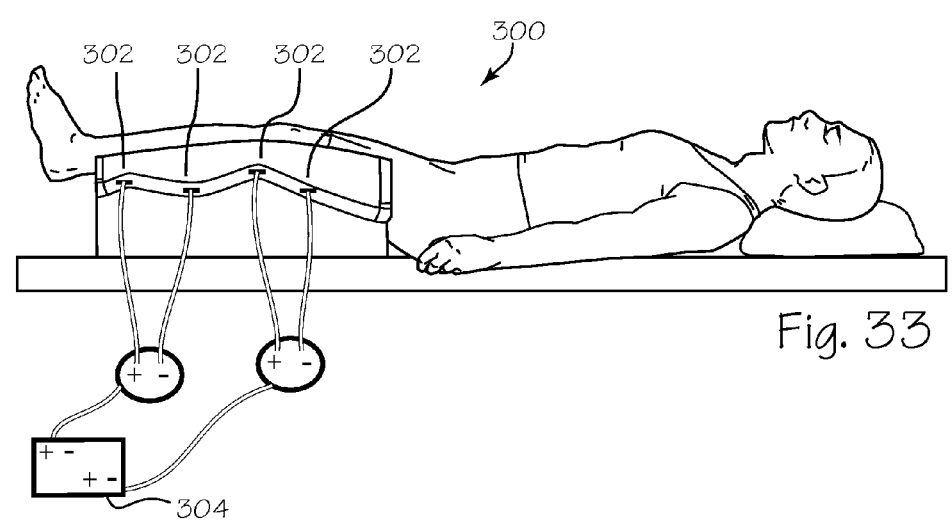
FIG. 33 illustrates a side elevational view of an embodiment of a device in accordance with the present invention, under a patient's legs.
Figure 34:
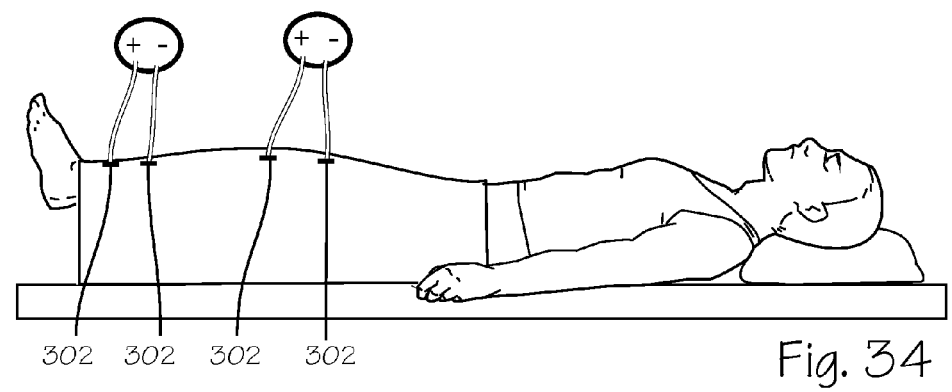
FIG. 34 illustrates a side elevational view of an embodiment of a device in accordance with the present invention, over a patient's legs.
Figure 35:
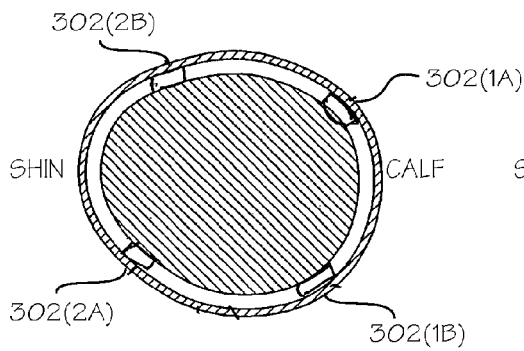
FIGS. 35 and 36 illustrate cross-sectional views, taken a line A-A in FIG. 10, showing several features of other embodiments of the invention.
Figure 36:
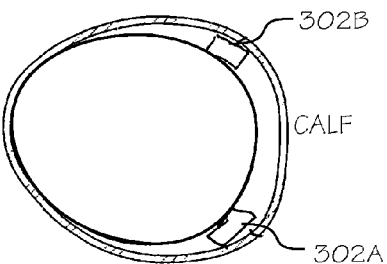

According to yet further principles of the invention, counter-stimulation for treatment of RLS can be produced by electrical nerve stimulation, muscle stimulation, or both. With reference to FIGS. 33 and 34, an exemplary embodiment 300 includes a series of sensors and/or electrodes 302 which are activated for muscle stimulation, nerve stimulation, or both. When activated for muscle stimulation, the voltage and frequency of the electrical energy applied to the patient is sufficient to cause muscular contraction, which provides the counter-stimulation to RLS; when activated for nerve stimulation, the electrical energy applied to the patient is sufficient to cause a patient's nerve to be stimulated. For either or both of these purposes, the electrodes and/or sensors are driven by a controller 304, which controls the application of voltage or current to the electrodes 302, and which may be a simple timer, a complex controller, or other such device. With reference to the exemplary embodiments illustrated in FIGS. 35 and 36, multi-circuit (circuits 1, 2; electrodes A, B of each circuit) stimulation can be applied circumferentially around the, e.g., leg of the patient, axially, e.g., up and down along the length of the patient's leg, or both, using sets of electrodes 302. Alternatively, single circuit (A, B) stimulation can be applied laterally and/or axially, as suggested in FIG. 36.

Figure 37:
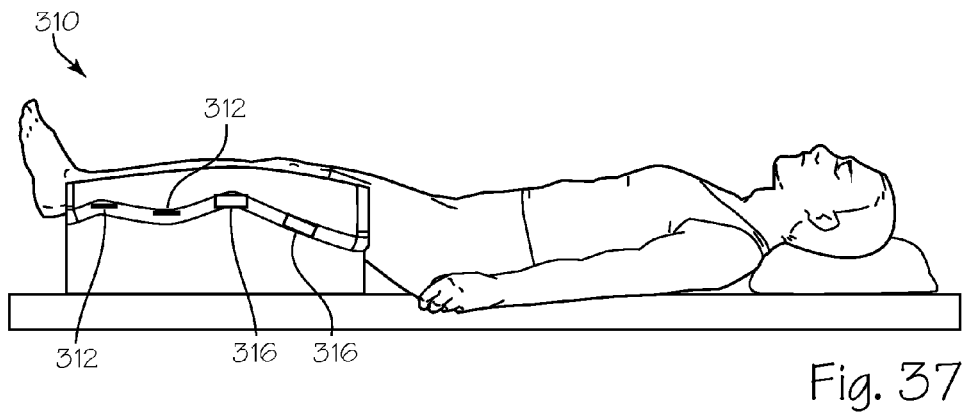
FIG. 37 illustrates a side elevational view of an embodiment of a device in accordance with the present invention, under a patient's legs.
Figure 38:
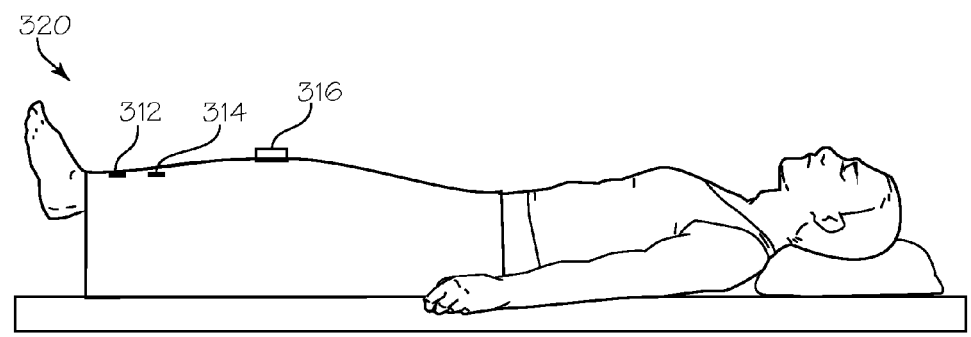
FIG. 38 illustrates a side elevational view of an embodiment of a device in accordance with the present invention, over a patient's legs.

According to yet further principles of the invention, counter-stimulation for treatment of RLS can be produced by the application of temperature changes, e.g., hot, cold, and/or alternating hot and cold, to the patient. With reference to an exemplary embodiment 310 illustrated in FIG. 37, a resistance heating element 312, Peltier device 314, and/or a bladder 316 containing heating or chilling fluid is positioned on the skin surface, below the patient, and an associated (and unillustrated) control device controls application of heat and/or cold to the patient's skin. In FIG. 38's embodiment 320, the heat transfer device 312, 314, 316 is positioned on top of the patient, mounted to a blanket or the like. FIGS. 39 and 40, which are illustrations of cross-sectional views similar to other figures herein, show series of Peltier 314 devices to heat, cool, and/or alternate hot/cold to the patient around a circumference of a, e.g., limb, or a single device can be provided. Optionally, a series of fluid bladders 316 can be provided for holding and/or circulating hot or cold fluid, e.g., water. Alternately, a series of resistive heating pads 312 can be provided.

According to further principles of the invention, counter-stimulation for treatment of RLS can be produced by application of a chemical to the patient's skin. With reference to FIG. 41, an exemplary embodiment 330 includes localized ports 332 or a porous membrane 334 positioned on the patient's skin, to dispense a preselected chemical, thus causing sensory stimulation. With reference to FIGS. 42 and 43, one or more chemicals can be input to a bladder 336 or diffuser, and provided in either a pulsatile or continuous flow. A bladder/diffuser, when used, can dispense a chemical such as Bengay™, capsaicin, or DMSO, which provides an exotherm on dissolving into the skin. As indicated in these figures, the chemical application can be completely circumferential, or locally, non-circumferentially applied, where the bladder acts as a manifold for the chemical.

Figure 45:
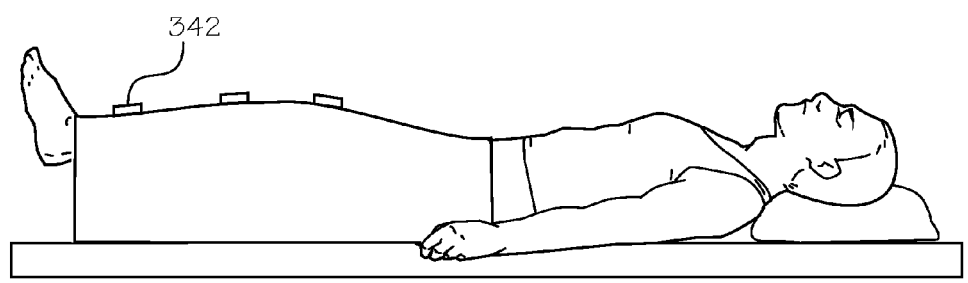
FIG. 45 illustrates a side elevational view of an embodiment of a device in accordance with the present invention, over a patient's legs.
Figure 46:
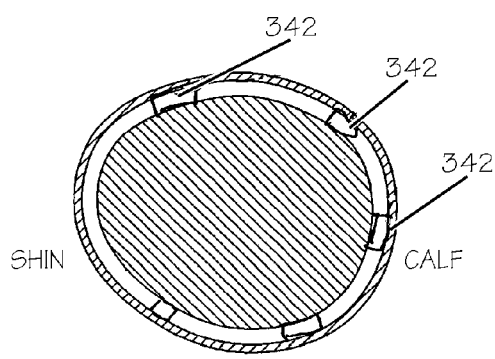
FIGS. 46 and 47 illustrate cross-sectional views, taken a line A-A in FIG. 10, showing several features of other embodiments of the invention.
Figure 47:
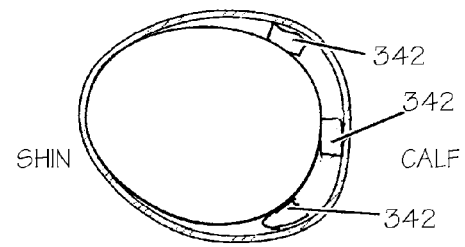

According to further principles of the invention, counter-stimulation for treatment of RLS can be produced by application of magnetic fields to a portion of the patient. With reference to an exemplary embodiment 340 illustrated in FIGS. 44 and 45, one or more electromagnets 342 are positioned close enough to the patient for the magnetic field to produce a counter-stimulation. A controller, not illustrated, is provided to control the operation of the electromagnets, that is, to turn them on and off, alternate the current direction, rotating fixed pole magnets within a housing, or combinations thereof. Electromagnets, rotating fixed pole magnets, or either of these could be sequenced to give some vibration or touch sensation, if desired. As illustrated in the cross-sectional views of FIGS. 46 and 47, electromagnets 342 can be positioned either circumferentially around a portion of the patient's body, or only on one side. In general terms, however, magnets can be provided which are: electromagnets which are turned on and off to pulse a localized magnetic field; rotating, fixed pole magnets which are rotated in a housing; and/or a magnetic button or malleable magnetic rod.

Figure 49:
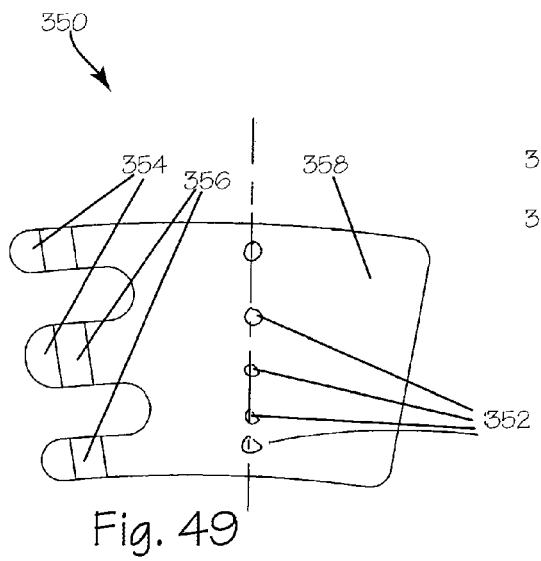
FIGS. 48 and 49 illustrate yet another embodiment of a device for RLS counter-stimulation.
Figure 48:
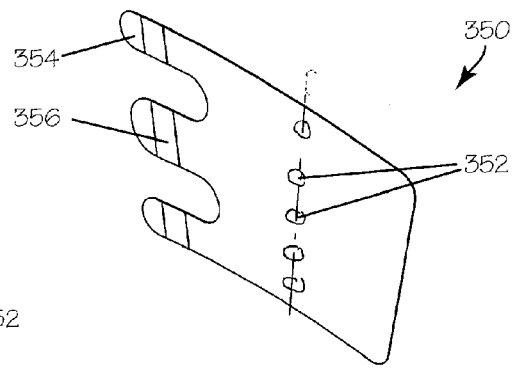
Figure 51:
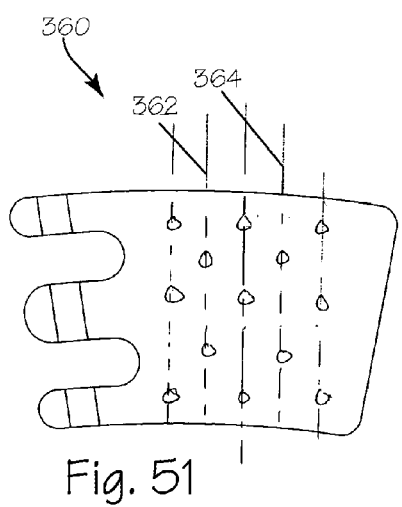
FIGS. 50 and 51 illustrate another embodiment of a device for RLS counter-stimulation.
Figure 50:
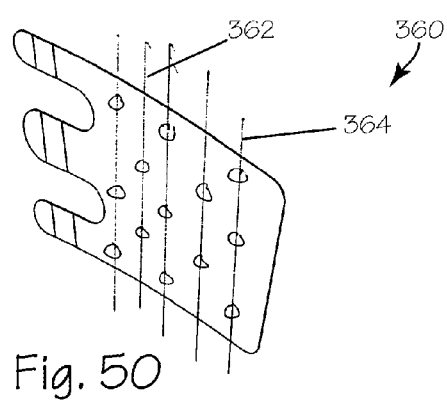
Figure 52:
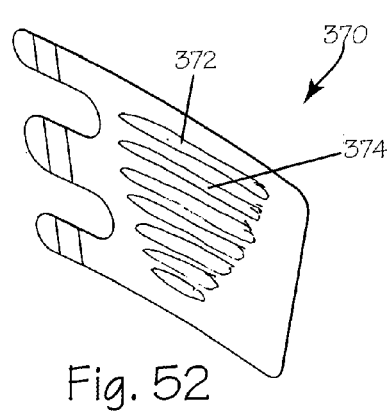
FIGS. 52 and 53 illustrate yet another embodiment of a device for RLS counter-stimulation.
Figure 53:
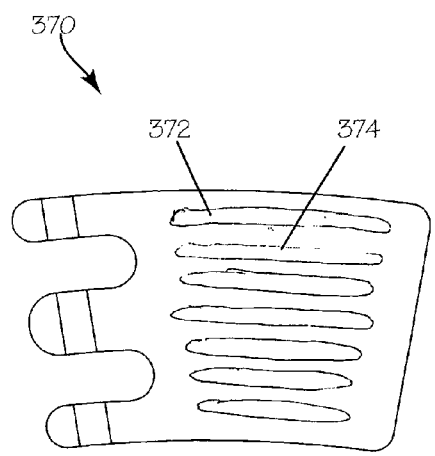
Figure 54:
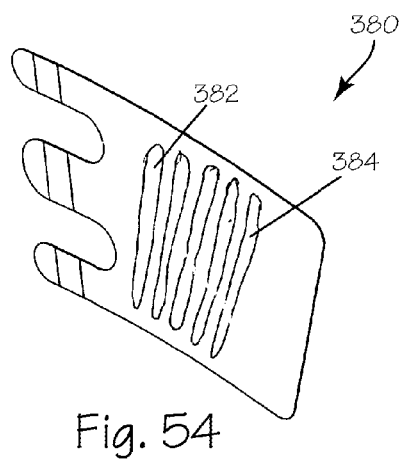
FIGS. 54 and 55 illustrate another embodiment of a device for RLS counter-stimulation.
Figure 55:
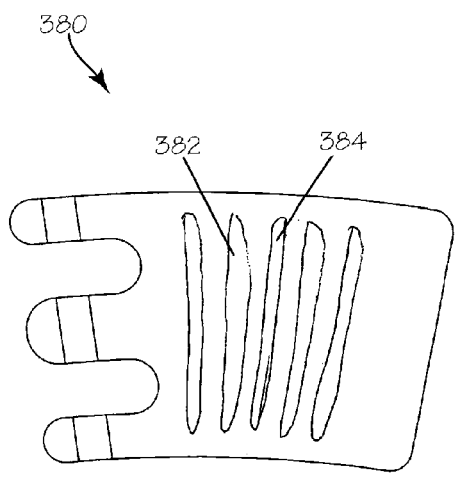

FIGS. 48 and 49 illustrate yet a further embodiment 350 in accordance with principles of the present invention. One or multiple sensory input drivers 352 are positioned in a line on a wrap 358, sized so that the line of sensors can be positioned along a predetermined portion of the patient's body. By way of a non-limiting example, the wrap is sized to fit around an adult human's calf or thigh, and includes fasteners 356 on respective portions 354 of the wrap so that the wrap can be held onto the patient (e.g., hook-and-loop-pile-type fasteners, e.g., Velcro-brand fasteners, magnetic strips, hook-and-eye fasteners, snaps, laces, etc.) with the sensors in sufficient contact with the patient to perform their respective sensing and/or stimulation function. Alternatively, as illustrated in FIGS. 50 and 51, another exemplary embodiment 360 includes two or more lines 362, 364 of sensors, or the same or different types, can be provided in the wrap. FIGS. 52 and 53 illustrate an embodiment 370 in which the stimulator(s)/sensor(s) are positioned in circumferential bands 372, 374, while the exemplary embodiment 380 illustrated in FIGS. 54 and 55 includes axial bands 382, 384 of stimulator(s)/sensor(s).

The sensory input drivers described herein are connected to a controller (not illustrated) which includes logic, either in one or more electronic circuits, or in a set of logical instructions which are provided in a memory, and with a processor which can access the memory and execute the set of instructions based on the signals received from the sensory input drivers, to drive one or more of the devices described herein to create a counter-stimulus for RLS.

FIGS. 56 and 57 illustrate an example of a device 390 embodying principles of the present invention. A plurality of DC motors 394 are positioned on or in a foam (e.g., polyurethane foam) body 392, which is advantageous, yet optionally, flexible, optionally with an outer jacket 396 of, e.g., neoprene. The motors are each connected to a relay which receives a control signal from a suitable controller. The controller provides a signal to the relay to actuate the motors for a predetermined duty cycle. For example, the duty cycle could be that the motors are on for between 1 and 180 seconds, and off for between 1 and 18 seconds. As described above, the motors, when supplied with electricity during an "on" portion of a cycle, turn to produce a counter-stimulation, e.g., by having the motor produce mechanical vibration.

Figure 58:
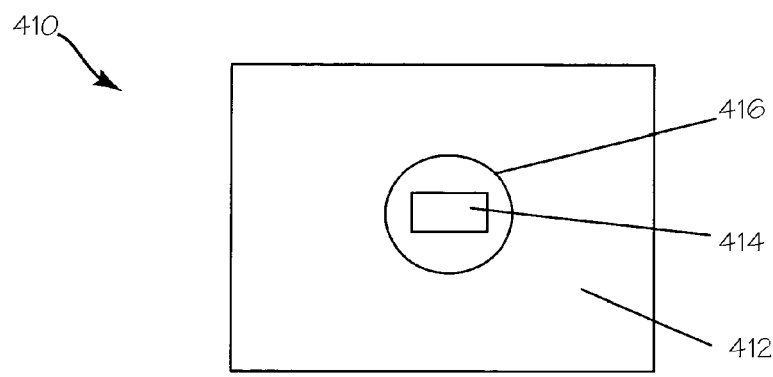
FIGS. 58 and 59 illustrate yet another embodiment of a device for RLS counter-stimulation.
Figure 59:
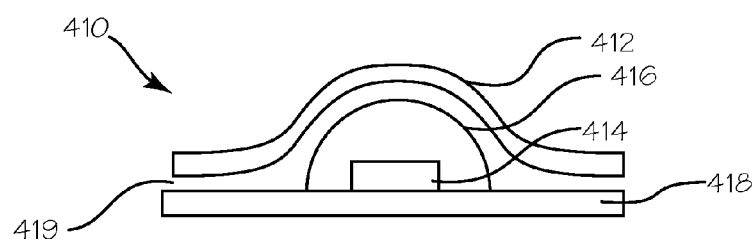

FIGS. 58 and 59 illustrate yet another exemplary embodiment 410, in which an electric motor 414, fed by a voltage source via leads 419, is encapsulated in a flexible material 412, 418, e.g., neoprene, with a hemispherically shaped cover 416 over the motor; when actuated, as described herein, the motor produces a counter-stimulation that can be felt by the patient through the underlying neoprene 418.

FIG. 60 illustrates yet another exemplary embodiment 400 of a simple cage or jack device which can be used to produce a counter-stimulation. An actuator rod 406 extends through a set of links 402 joined together at pivots 404, with the actuator rod connected to an end pivot on an end of the device opposite where the actuator rod extends through a slide pivot 408; alternatively, the rod can be a screw, and the slide replaced with a nut. Motion of the rod 406 (suggested by the double-ended arrow) through the slide 408 pulls the end pivot toward the slide pivot, causing the links 402 of the cage to move at their pivots 404 and push the upper link up, relative to the lower link, as suggested by the arrow. By positioning the cage device 400 adjacent to the skin of a patient, and connecting the actuator rod 406 to a linear actuator controlled by a controller (neither illustrated), pressure and/or vibration can be applied to the patient as a counter-stimulation to RLS.

In general terms, mechanical vibration used as a counter-stimulation to RLS advantageously is in a range of frequencies between about 50 Hz to 10 per minute, with amplitudes which can be frequency-dependent, ranging from about 0.002 inches to about 0.75 inch in amplitude. While other frequencies and amplitudes can be used, these ranges are preferred. Determining the best combination of frequency and amplitude of the mechanical vibration for a particular patient can be easily performed by simple trial and error.

In general terms, temperature cycling used as a counter-stimulation to RLS advantageously is in a range for heating the pad or sensor from the ambient skin temperature up to about 106° F., although temperatures up to 120° F. can also be beneficial. For cooling, the pad/sensor is at a temperature from about ambient skin temperature down to 62° F., although a temperature as low as 52° F. can also be beneficial. One exemplary cycle could include the following: from ambient temperature, heat to skin to a target temperature (e.g., 106° F.) within 2-20 seconds; hold the temperature at the target temperature for 2-20 seconds; and then cool, either passively or actively, down to ambient temperature; and rest for between 2 seconds and one minute. Another exemplary cycle could include the following: from ambient temperature, cool to skin to a target temperature (e.g., 62° F.) within 2-20 seconds; hold the temperature at the target temperature for 2-20 seconds; and then heat, either passively or actively, up to ambient temperature; and rest for between 2 seconds and one minute. The total cycle time can be between about 6 second to 90 seconds for ramping up the temperature, maintaining temperature, and ramping down, with a "rest" period of 2 seconds to one minute.

In general terms, tissue massaging used as a counter-stimulation to RLS advantageously is effected with a contact surface against the skin of the patient which is domed, e.g., hemispherical, with an outer diameter between about 0.5 inch and 1.0 inch, and with a linear motion into the patient's skin of between 0.01 inches and 1.5 inches. While this motion can be controlled with a stepper motor to control motion and flexibility of the design, other devices can also be used. The deflection time of, e.g., the jack illustrated in FIG. 60, should be from 0.5 seconds to 5 seconds, with a hold time of between about 1 and 10 seconds, a relaxation deflection time of 0.5 to 5 seconds, and a rest time of 1 to 30 seconds.

More timing functions, particularly for continuous, low-amplitude vibration, and starting and stopping the vibration for varied periods of time, is also beneficial. By way of a non-limiting example, a timing relay can be used to cycle vibrating motors on and off, with timing cycles ranging from 1 second to 180 seconds on, and "off times" ranging from several seconds to 3 minutes. Typical, however, times for use are 30 seconds on, with a 5 to 10 second off period. The relay cycles in this manner for 5 minutes to relieve symptoms, although up to 20 minutes of cycling can be used to alleviate RLS symptoms completely through the night.

Whether vibration, heat, cold, or massage, a range of operation from 5 minutes to 30 minutes should be sufficient to act as a counter-stimulation for many patients. At the end of cycling, a ramp down in intensity of the stimulation may also be beneficial, so as not to waken or alarm the patient due to sudden stoppage which might reawaken the patient if they have fallen back asleep. The counter-stimulating vibration may be applied to the patient when the patient is awake, at a level which allows the patient to fall asleep, and insufficient to prevent the patient from falling asleep.

Figure 61:
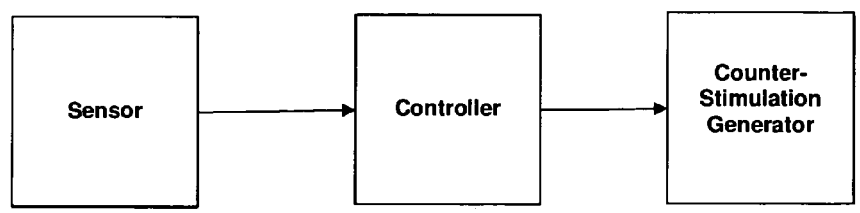
FIG. 61 illustrates an exemplary system for RLS counter-stimulation.

FIG. 61 illustrates a highly schematic view of a relationship between one or more sensor(s), one or more controller(s), and one or more counter-stimulation generators embodying principles of the invention. As described herein, one or more sensors are in sufficient proximity to a sufferer of RLS that it can sense a body condition of the patient indicative of an RLS episode. The sensor(s) generates and transmits a signal to the controller(s), which could be wired or wirelessly connected. The controller includes logic, embodied either in one or more electronic circuits, or in a set of logical instructions which are provided in a memory. When provided in a memory, the controller(s) include a processor which can access the memory and execute the set of instructions based on the signals received from the sensor(s), to generate an output signal. The controller(s) are in communication (wired or wireless) with the counter-stimulation generators, as described throughout this disclosure, to drive one or more of the generators to create a counter-stimulus for RLS. Because the details of the controller's construction are well within the skill of the ordinary routineer, they are not provided here so as to not obscure other aspects of the invention.

Figures 62, 63:
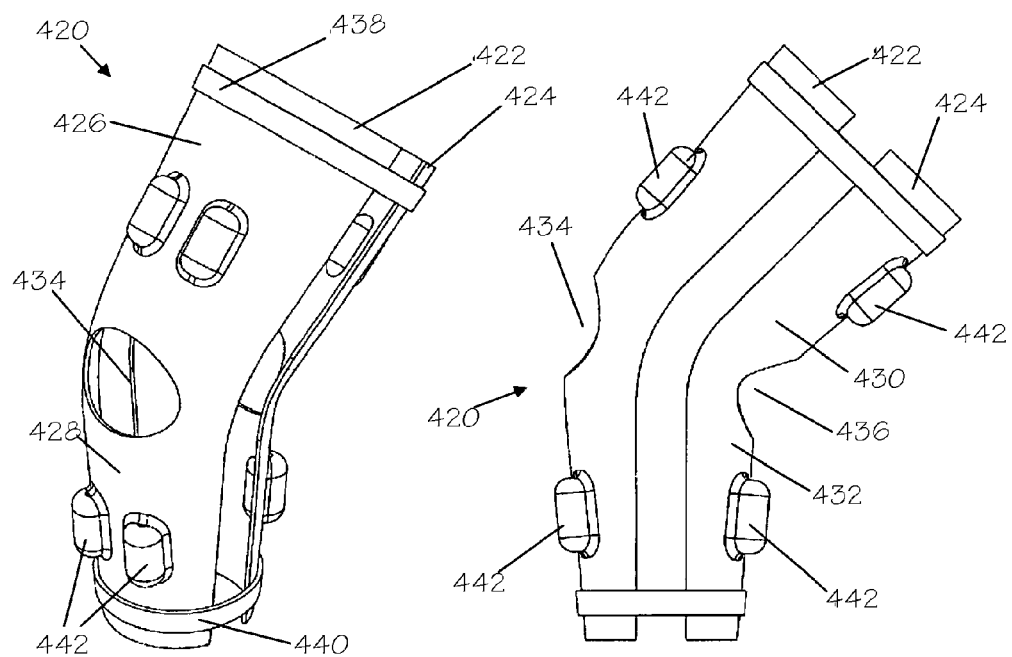
FIGS. 62 and 63 illustrate yet another embodiment of a device for RLS counter-stimulation.

FIGS. 62 and 63 illustrate yet another exemplary embodiment 420 of a RLS counter-stimulation device embodying principles of the present invention. In general terms, the device 420 includes a removable sleeve to which at least one, and advantageously, yet optionally, multiple counter-stimulation devices are mounted. The sleeve is configured so that it can be worn by a RLS-sufferer, and more particularly on the sufferer's limb. While the exemplary device 420 is configured to be easily worn around an arm or leg, at the elbow or knee, respectively, the device 420 is not so limited and can be differently configured so that it can be worn around other parts of the sufferer's body so as to bring the counter-stimulation device(s) into contact with that portion of the body at which counter-stimulation is most effective against RLS.

Turning back to the drawing figures, the exemplary device 420 includes a front shell 422 and a rear shell 424, one or both formed of a relatively stiff, preferably polymeric material, e.g., polyethylene or polypropylene; when only one of the shells is formed of the stiff material, the other can be formed of a flexible material, or can be not included at all in the device. The front shell 422 includes upper 426 and lower 428 portions, while the rear shell 424 similarly includes upper 430 and lower 432 portions. The upper and lower portions of the shells are advantageously separated by openings 434, 436, the front opening 434 being sized to be capable of receiving an kneecap (patella) or elbow therethrough. When configured to be worn by a patient's leg or arm, the shells are formed at an angle (see FIG. 63) between the upper and lower portions, so that the leg or arm is comfortably bent when wearing the device 420. The shells 422, 424, when two shells are provided, are held together and to the patient by at least one, and preferably a pair of bands 438, 440, positioned at the top and bottom of the shell(s). The band can be simple elastic bands, or are more preferably adjustable, e.g., including hook-and-loop-pile type or other fastener systems (e.g., Velcro), so that the device 420 can be adjusted to the patient.

At least one, and advantageously several counter-stimulation devices 442 are attached or mounted to the shells 422, 424. The counter-stimulation devices 442 can take any of the forms described herein. In one embodiment, the counter-stimulation device 442 is one that produces mechanical vibrations, and can either be in contact with the patient's skin through the inside surface of the shells 422, 424, or can also vibrate the entire shell 422, 424, to produce counter-stimulation. The embodiment illustrated in FIGS. 62 and 63 includes devices 442 on both the front 422 and rear 424 shells, and the upper and lower portions thereof; more or fewer devices 442 can be provided as needed for any particular patient in order to create an adequate counter-stimulation vibration. The controllers and energy sources which drive the devices 442 are not illustrated so as to not obscure aspects of the invention.

Figures 64, 65:
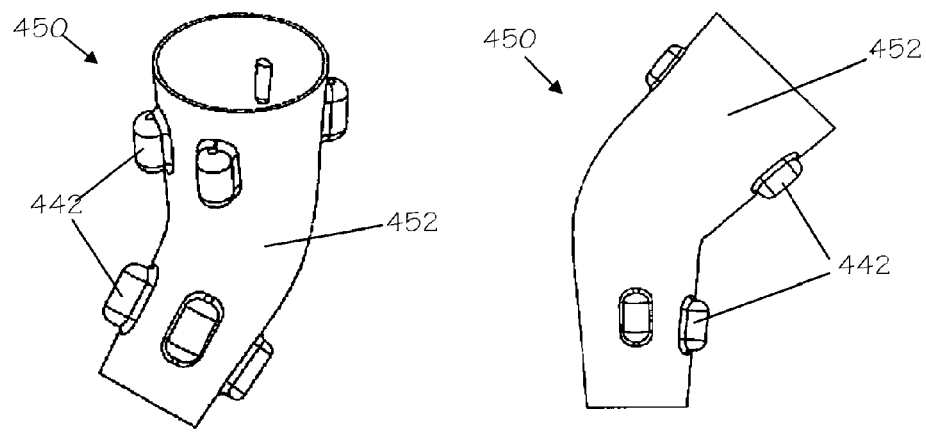
FIGS. 64 and 65 illustrate yet another embodiment of a device for RLS counter-stimulation.
Figure 66:
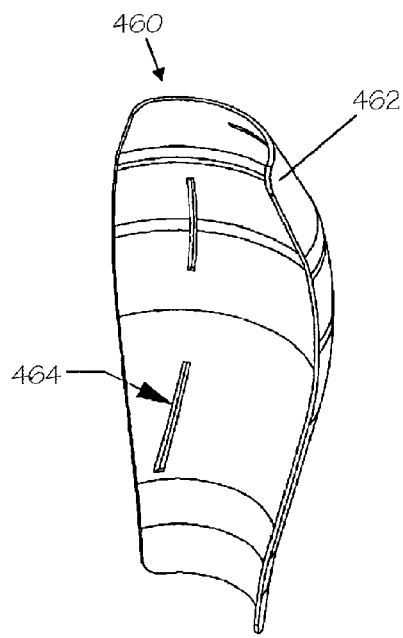
FIGS. 66-70 illustrate another embodiment of a device for RLS counter-stimulation.
Figure 67:
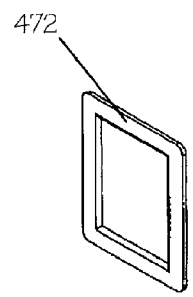
Figure 68:
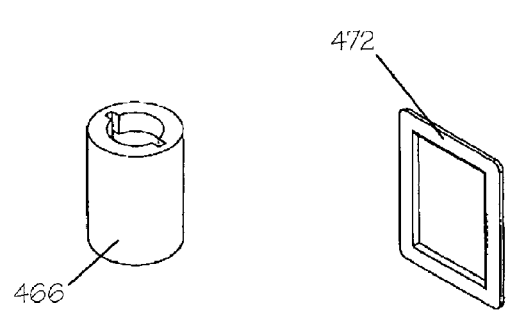
Figure 69:
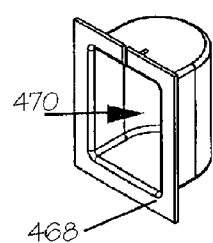
Figure 70:
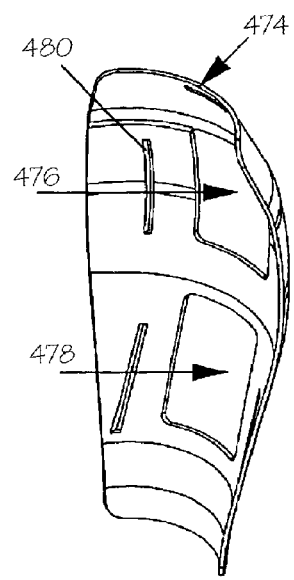

FIGS. 64 and 65 illustrate embodiments 450 similar in many respects to those illustrated in FIGS. 62 and 63, except that the devices 442 are mounted to a flexible sleeve 452, e.g., Neoprene, Lycra, a knit fabric, or the like, which can stretch and confirm to an arm or leg, with pockets formed in the sleeve in which the devices 442 are received. The sleeve can be straight or, as illustrated, preformed at a comfortable angle.

FIGS. 66-70 illustrate yet another device 460 embodying principles of the present invention. When the locus of counter-stimulation for a patient suffering from RLS is advantageously applied to the patient's calf, the device 460 is adapted to be worn by the patient on the calf so that counter-stimulation be applied there. The device 460 includes a rigid shell 474 which is elongate and concave in the shape of a person's calf, with a correspondingly shaped flexible liner 462. The liner 462 and the shell 474 can include structures which allow the device 460 to be adjustably worn by the patient; in the embodiment illustrated, slits 464, 480 are provided for the passage of (unillustrated) straps, however other structures can be used in addition or instead. The shell 474 includes one or more holes, cutouts, or windows 476, 478, through which at least one, and optionally multiple counter-stimulation devices are attached to the shell. In the exemplary embodiment illustrated, the counter-stimulation device is a mechanical vibration device, here a motor and housing 466 are received in the seat 470 of a motor shell 468, with one or more optional spacers or shims 472 positioned between the housing 466, shell 474, and liner 462. With the shells 468 extending outward through the hole 476, 478, the motor 466 vibrates the device 460 and/or the adjacent patient's skin, causing a counter-stimulation to RLS. According to another embodiment, the shell 474 can be formed in the well known shape of a shinguard and worn one the patient's shin.

FIGS. 71-73 illustrate an exemplary embodiment of a device 490 which can produce mechanical vibrations suitable for use as a counter-stimulation to RLS in any of the other embodiments described herein. The device 490 includes a housing 492 in the open interior of which an electric motor 494 is received. The motor 494 includes a shaft 504 extending from the motor, which rotates when the motor is energized. A motor cap 496 is positioned around the shaft to retain the motor in the housing 492. A counterweight 498 having a throughhole 502 is mounted on the shaft 504; the hole is offset from the center of mass of the counterweight so that, when rotated, the counterweight creates a vibration. When the counterweight is cylindrical, as illustrated, the hole is therefore offset from the center axis of the cylinder; when the counterweight has another shape or uneven mass distribution, the hole is offset from the center of mass of the counterweight.

For some patients, effective counters-stimulation to RLS symptoms include mechanical stimulus at low frequencies, for which a rotating motor with an eccentric weight may not provide adequate relief. For such patients, the present invention also includes a solenoid, a geared mechanical actuator, or a cam lobe that are rotated or otherwise actuated to produce a low frequency, e.g., 1 to 20 Hz. Additionally, a brushless motor may be a requirement for the medical devices described herein, as the RF emissions for the brushes and the motor moving within its own magnetic field may be dangerous for patients with pacemakers or implantable defribrillators, were a motor with brushes used. Also, the smaller controllers and drive circuitry are sensitive to induced noise, so extreme filtering or shielding would be required to produce an adequately safe device for this purpose.

In a highly simplified form, systems embodying principles of the present invention include a simple on/off button or switch (not illustrated) which can be actuated by the patient when desired to generate a counter-stimulation to RLS symptoms. When actuated, the button simply communicates a signal to the controller to begin generating the counter-stimulation. More complex embodiments include sensors in addition to or instead of an on/off button, which sensors are mounted in positions relative to the patient to sense conditions indicative of RLS symptoms, and to communicate signals to the controller that the generation of counter-stimulation is indicated. As such sensors are well known to those of ordinary skill in the art, a detailed description thereof will not be presented herein so as to not obscure aspects of the invention.

While the invention has been described in detail with reference to exemplary embodiments thereof, it will be apparent to one skilled in the art that various changes can be made, and equivalents employed, without departing from the scope of the invention. The foregoing description of the preferred embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

We claim:

1. A system for generating a counter-stimulation in a patient suffering from restless leg syndrome, the system comprising:
   a vibration generator configured and arranged to generate a counter-stimulation vibration in a patient suffering from restless leg syndrome, the counter-stimulation having a frequency of between 50 hz and 10 per minute and of an amplitude and time duration either lower than that which would wake the patient and higher than that sufficient to relieve restless leg syndrome symptoms, or sufficient to relieve restless leg syndrome symptoms and allow the patient to return to sleep;
   a controller configured and arranged to drive the vibration generator, the controller in communication with the vibration generator, the controller being configured and arranged to ramp down the counter-stimulation so as not to waken or alarm the patient; and
   a base configured and arranged to hold the vibration generator adjacent to a patient, the vibration generator attached to the base.

2. The system according to claim 1, wherein the vibration generator comprises a device selected from the group consisting of a piezo-chip, a loudspeaker, a motor with an eccentric weight, and a solenoid.

3. The system according to claim 2, wherein the vibration generator comprises an electric motor having a shaft, and a weight having a hole therein, the weight positioned on the shaft, the hole located at a position offset from a center of mass of the weight.

4. The system according to claim 3, further comprising: a housing attached to the base; and wherein the weight is located in the housing.

5. The system according to claim 1, wherein the base comprises a flexible sheet.

6. The system according to claim 5, wherein the sheet comprises a foam sheet, the vibration generator positioned in the foam sheet.

7. The system according to claim 1, wherein the base comprises a rigid shell having at least one housing, the vibration generator located in the housing.

8. The system according to claim 7, wherein the vibration generator comprises a mechanical vibrator.

9. The system according to claim 7, wherein the rigid shell comprises a hole sized and adapted to receive the kneecap of the patient.

10. The system according to claim 7, wherein the rigid shell is shaped to at least in part conformingly fit over the thigh of the patient.

11. The system according to claim 7, wherein the rigid shell is shaped to conformingly fit over the calf of the patient.

12. The system according to claim 1, wherein the base comprises a flexible and elastic sleeve having at least one pocket, the vibration generator positioned in the at least one pocket.

13. The system according to claim 1, further comprising: a plurality of vibration generators attached to the base and in communication with the controller.

14. A method of treating restless leg syndrome, the method comprising:
   selecting a patient experiencing restless leg syndrome;
   vibrating a portion of the patient with a vibration generator at a frequency of between 50 hz and 10 per minute during a restless leg syndrome episode at an amplitude and duration sufficient to act as a counter-stimulation vibration to said restless leg syndrome episode and either to allow the patient to return to sleep or to not wake a sleeping patient; and
   ramping down the counter-stimulation vibration so as not to waken or alarm the patient.

15. The method according to claim 14, wherein said patient is asleep; and wherein said vibrating is insufficient to wake the patient.

16. The method according to claim 14, wherein the patient is awake; and wherein said vibrating is insufficient to prevent the patient from falling asleep.

17. The method according to claim 14, wherein said vibrating comprises vibrating with an electric motor.

18. A method of treating restless leg syndrome, the method comprising:
   selecting a patient experiencing restless leg syndrome;
   vibrating a portion of the patient with a vibration generator at a frequency of between 50 hz and 10 per minute during a restless leg syndrome episode at an amplitude and duration sufficient to act as a counter-stimulation vibration to said restless leg syndrome episode and either to allow the patient to return to sleep or to not wake a sleeping patient; and
   initiating said vibrating step at the onset of an episode of restless leg syndrome symptoms; and
   ramping down the counter-stimulation vibration so as not to awaken or alarm the patient.

19. The method according to claim 18, wherein counter-stimulating vibration is initiated while the patient is awake; and wherein said vibrating is insufficient to prevent the patient from falling asleep.

20. A method of treating restless leg syndrome, the method comprising:
   selecting a patient experiencing restless leg syndrome;
   vibrating a portion of the patient with a vibration generator at a frequency of between 50 hz and 10 per minute at an amplitude, and duration sufficient to act as a counter-stimulation vibration to restless leg syndrome but low enough to allow the patient to sleep; and
   initiating said stimulating step at the onset of an episode of restless leg syndrome symptoms; and
   ramping down the counter-stimulation vibration so as not to awaken the patient.

21. The method according to claim 20, wherein counter-stimulating vibration is initiated while the patient is awake; and wherein said vibrating is insufficient to prevent the patient from falling asleep.

22. A method of treating restless leg syndrome, the method comprising:

selecting a patient experiencing restless leg syndrome;

vibrating a portion of the patient with a vibration generator at a frequency of between 50 hz and 10 per minute at an amplitude and duration sufficient to act as a counter-stimulation vibration to restless leg syndrome but low enough to allow the patient to sleep; and performing said stimulating step while (1) the patient is attempting to sleep and (2) while the patient is experiencing symptoms of restless leg symptoms; and ramping down the counter-stimulation vibration so as not to awaken the patient.

23. The method according to claim 22, wherein counter-stimulating vibration is initiated while the patient is awake; and wherein said vibrating is insufficient to prevent the patient from falling asleep.

24. A method of treating restless leg syndrome, the method comprising:

selecting a patient experiencing restless leg syndrome;

applying a counter-stimulation generation device to a leg of the patient, said counter-stimulation generation device comprising a vibration generator, a controller operable to drive the counter-stimulation generation device, and a sleeve or pad for holding the vibration generator, said vibration generator operable to generate a counter-stimulation having a frequency of between 50 hz and 10 per minute of an amplitude, and time duration sufficient to relieve restless leg syndrome symptoms but low enough to allow the patient to sleep;

operating the counter-stimulation generation device to provide counter-stimulating vibration to the legs of the patient, at the onset of a restless leg syndrome episode;

ramping down the counter-stimulation vibration after a period of 5 to 30 minutes of counter-stimulation vibrations.

25. The method according to claim 24, wherein counter-stimulating vibration is initiated while the patient is awake; and wherein said vibrating is insufficient to prevent the patient from falling asleep.

* * * * *